US008727997B2

(12) United States Patent
Shelley et al.

(10) Patent No.: US 8,727,997 B2
(45) Date of Patent: May 20, 2014

(54) VOLUME STATUS MONITOR: PERIPHERAL VENOUS PRESSURE, HYPERVOLEMIA AND COHERENCE ANALYSIS

(75) Inventors: Kirk H. Shelley, New Haven, CT (US); David G. Silverman, West Redding, CT (US); Adam J. Shelley, Baltimore, MD (US)

(73) Assignee: Yale University, New Haven, CT (US)

( * ) Notice: Subject to any disclaimer, the term of this patent is extended or adjusted under 35 U.S.C. 154(b) by 692 days.

(21) Appl. No.: 12/580,648

(22) Filed: Oct. 16, 2009

(65) Prior Publication Data

US 2010/0191128 A1   Jul. 29, 2010

Related U.S. Application Data

(60) Provisional application No. 61/106,257, filed on Oct. 17, 2008, provisional application No. 61/159,621, filed on Mar. 12, 2009.

(51) Int. Cl.
*A61B 5/021* (2006.01)
*A61B 5/0295* (2006.01)

(52) U.S. Cl.
USPC ............ 600/485; 600/481; 600/504; 600/507

(58) Field of Classification Search
USPC .................................. 600/481–507
See application file for complete search history.

(56) References Cited

U.S. PATENT DOCUMENTS

| 5,396,893 | A | 3/1995 | Oberg et al. |
| 6,002,952 | A | 12/1999 | Diab et al. |
| 6,067,462 | A | 5/2000 | Diab et al. |
| 6,699,194 | B1 | 3/2004 | Diab et al. |
| 6,709,402 | B2 | 3/2004 | Dekker |
| 7,001,337 | B2 | 2/2006 | Dekker |
| 7,471,971 | B2 | 12/2008 | Diab et al. |

(Continued)

FOREIGN PATENT DOCUMENTS

| DE | 19650738 | 6/1998 |
| WO | WO 98/24489 | 6/1998 |

OTHER PUBLICATIONS

Shelley et al. "What is the best site for measuring the effect of ventilation on the pulse oximeter waveform?" Anesth Analg. Aug. 2006;103(2):372-7.*

(Continued)

*Primary Examiner* — Navin Natnithithadha
*Assistant Examiner* — Meredith Weare
(74) *Attorney, Agent, or Firm* — McCarter & English, LLP

(57) ABSTRACT

Systems and methods are provided for monitoring changes in blood volume using waveforms in the peripheral vasculature. In particular, the systems and methods relate to detecting ventilation-induced variation (VIV) of waveforms in the peripheral vasculature. Advantageously, the systems and methods may relate to analyzing VIV in peripheral venous pressure (PVP). Thus, the VIV of PVP may be measured, wherein decreased VIV is indicative of decreased blood volume In exemplary embodiments, such as involving spontaneous breathing, it may be necessary to account for changes in respiratory signal strength. Thus systems and methods are also provided for assessing coherence between ventilation and VIV for a flow or pressure waveform. Specifically, coherence is evaluated by comparing the waveform to a detected respiratory signal. Finally, systems and method are provided for distinguishing the impact of respiration on the PG signal during hypervolemia as compared to hypovolemia. Such systems and methods may advantageously be utilized to monitor fluid status during fluid replacement.

22 Claims, 14 Drawing Sheets

(56) References Cited

U.S. PATENT DOCUMENTS

| | | | |
|---|---|---|---|
| 7,489,958 | B2 | 2/2009 | Diab et al. |
| 7,499,741 | B2 | 3/2009 | Diab et al. |
| 8,556,818 | B2 * | 10/2013 | Joeken .......................... 600/484 |
| 2006/0241506 | A1 | 10/2006 | Melker et al. |
| 2006/0281983 | A1 | 12/2006 | Al-Ali et al. |
| 2007/0016031 | A1 | 1/2007 | Mourad et al. |
| 2007/0032732 | A1 | 2/2007 | Shelley et al. |
| 2008/0033306 | A1 * | 2/2008 | Joeken .......................... 600/485 |
| 2008/0081961 | A1 | 4/2008 | Westbrook et al. |
| 2009/0043179 | A1 | 2/2009 | Melker et al. |
| 2009/0069647 | A1 | 3/2009 | McNames et al. |
| 2009/0076399 | A1 | 3/2009 | Arbel et al. |
| 2010/0130874 | A1 * | 5/2010 | Joeken .......................... 600/485 |

OTHER PUBLICATIONS

"Coherence." Wikipedia. http://en.wikipedia.org/wiki/Coherence_(statistics).*
Nilsson et al. "Respiration can be monitored by photoplethysmography with high sensitivity and specificity regardless of anaesthesia and ventilatory mode." Acta Anaesthesiol Scand 2005; 49: 1157-1162.*
Rosolowsky, Erik W. "The Spectral Correlation Function—A New Tool for Analyzing Spectral Line Maps." Jul. 21, 1998. 49 pages.*
"Spectral Analysis." Jun. 23, 2004. http://web.archive.org/web/20040603144911/http://www.mathworks.com/access/helpdesk/help/toolbox/signal/signal.shtml.*
Nilsson et al. "Combined photoplethysmographic monitoring of respiration rate and pulse: a comparison between different measurement sites in spontaneously breathing subjects." Acta Anaesthesiol Scand 2007; 51: 1250-1257.*
Nilsson et al. "Respiratory variations in the reflection mode photoplethysmographic signal. Relationships to peripheral venous pressure." Medical & Biological Engineering & Computing 2003, vol. 41: 249-254.*
Nilsson et al. "Age and Gender Do Not Influence the Ability to Detect Respiration by Photoplethysmography." Journal of Clinical Monitoring and Computing (2006) 20:431-436.*
Hertzman, The Blood Supply of Various Skin Areas as Estimated by the Photoelectric Plethysmograph, Am. J. Physiol. 124: 328-340 (1938).
Cournand, et al., Physiological Studies Of The Effect Of Intermittent Positive Pressure Breathing On Cardiac Output In Man, AmJ Physio 1948; 152:162-73.
Brecher, et al., Effect Of Respiratory Movements On Superior Cava Flow Under Normal And Abnormal Conditions, Am J Physiol. 1953; 172:457-61.
Guyton, Determination Of Cardiac Output By Equating Venous Return Curves With Cardiac Response Curves, Physiol Rev. 1955; 35:123-9.
Bartelstone, Role Of The Veins In Venous Return, Circ Res. 1960; 8:1059-76.
Folkow, et al., Veins and Venous Tone, Am Heart J. 1964; 68:397-408.
Morgan, et al., The Homodynamic Effects Of Changes In Blood Volume During Intermittent Positive-Pressure Ventilation, Anesthesiology 1969; 30:297-305.
Eustace, A Comparison Between Peripheral and Central Venous Pressure Monitoring Under Clinical Conditions, Injury 1970.
Zoller, et al., The Role Of Low Pressure Baroreceptors In Reflex Vasoconstrictor Responses In Man, J Clin Invest. 1972; 51:2967-72.
Coyle, et al., Respiratory Variations In Systemic Arterial Pressure As An Indicator Of Volume Status, Anesthesiology 1983; 59:A53.
Jardin, et al., Cyclic Changes In Arterial Pulse During Respiratory Support, Circulation 1983; 68:266-74.
Perel, et al., Systolic Blood Pressure Variation Is A Sensitive Indicator Of Hypovolemia In Ventilated Dogs Subjected To Graded Hemorrhage, Anesthesiology 1987; 67:498-502.
Partridge, Use Of Pulse Oximetry As A Noninvasive Indicator Of Intravascular Volume Status, Journal of Clinical Monitoring 1987; 3:263-8.

Pizov, et al., Systolic Pressure Variation Is Greater During Hemorrhage Than During Sodium Nitroprusside-Induced Hypotension in Ventilated Dogs, Anesthesia & Analgesia 1988; 67:170-4.
Szold, et al., The Effect of Tidal Volume And Intravascular Volume State On Systolic Pressure Variation In Ventilated Dogs, Intensive Care Medicine 1989; 15:368-71.
Pizov, et al., The Use Of Systolic Pressure Variation In Hemodynamic Monitoring During Deliberate Hypotension In Spine Surgery, Journal of Clinical Anesthesia 1990; 2:96-100.
Perel A, Cardiovascular Assessment By Pressure Waveform Analysis, ASA Annual Refresher Course Lecture 1991:264.
Vincent, et al., Cascular Reactivity To Phenylephrine And Angiotensin II: Comparison Of Direct Venous And Systemic Vascular Responses, Clin Pharmocol Ther 1992; 51:68-75.
Rothe, Mean Circulatory Filling Pressure: Its Meaning And Measurement, J Appl Physiol. 1993; 74:499-509.
Shelley, Kirk H., et al.; "The Detection of Peripheral Venous Pulsation Using the Pulse Oximeter As A Plethysmograph," Journal of Clinical Monitoring, vol. 9 No. 4, pp. 283-287, 1993.
Lherm T, et al., Correlation Between Plethysmography Curve Variation ( Dpleth ) And Pulmonary Capillary Wedge Pressure ( Pcup ) In Mechanically Ventilated Patients , British Journal of Anesthesia 1995; Suppl. 1:41.
Dalen, et al., Is It Time To Pull The Pulmonary Artery Catheter?, JAMA 1996; 276:916-14.
Connors, et al., The Effectiveness Of Right Heart Catheterization In The Initial Care Of Critically Ill Patients, JAMA 1996; 276:889-97.
Rusch, et al., Signal Processing Methods For Pulse Oximetry, Computers in Biology and Medicine 1996; 26:143-59.
Murray, et al., The Peripheral Pulse Wave: Information Overlooked, Journal of Clinical Monitoring, vol. No. 12, No. 5, 1996, pp. 365-377, XP009104503.
Shelley, K. H., at al., "Arterial-Pulse Oximetry Loops: A New Method of Monitoring Vascular Tone," Journal of Clinical Monitoring, 13: 223-228, 1997.
Ornstein, et al., Systolic Pressure Variation Predicts The Response To Acute Blood Loss, Journal of Clinical Anesthesia 1998; 10:137-40.
Stack Jr., et al., Spectral Analysis Of Photoplethysmograms From Radial Forearm Free Flaps, Laryngoscope 1998; 108:1329-33.
Dorlas, et al., Photo-Electric Plythysmography As A Monitoring Device In Anaesthesia. Application And Interpretations, BR J Anaethesia 1999 82(2):178-81; A245, H188, H236.
Shamir, et al., Pulse Oximetry Plethysmographic Waveform During Changes In Blood Volume, British Journal Of Anaesthesia 82(2): 178-81 (1999).
Johansson, et al, Estimation Of Respiratory Volumes From The Photoplethysmographic Sit. Parti: Experimental Results, Medical and Biological Engineering and Computing 37(1): 42-7 (1999).
Munis et al., Reported Mean PVP Values of 13 mm Hg, CVP Values of 10 mm Hg, with a PVP-CVP Difference of 3 mm Hg (see Munis J.R., Bhatia et al., Peripheral Venous Pressure As Hemodynamic Variable In Neurosurgical Patients, Anesth Analg 2001; 91(1): 172-9).
Amar, et al., Correlation Of Peripheral Venous Pressure And Central Venous Pressure In Surgical Patients, J Cardiothorac Vasc Anesth. 2001; 15:40-3.
Awad, A.. A., M.D., et al., "Different Responses of Ear and Finger Pulse Oximeter Wave Form to Cold Pressor Test," Technology, Computing and Simulation, Anesthesia & Analgesia, 92: 1483-6, 2001.
Awad, A.. A., M.D., et al., "How Does the Plethysmogram Derived From the Pulse Oximeter Relate to Arterial Blood Pressure in Coronary Artery Bypass Graft Patients?", Anesthesia & Analgesia, 93: 1466-71, 2001.
Tyberg, How Changes In Venous Capacitance Modulate Cardiac Output, Pflugers Arch. 2002; 445:10-7.
Golparvar et al., Evaluating the Relationship Between Arterial Blood Pressure Changes and Indices of Pulse Oximetric Plethysmogtaphy, Anesthesia and Analgesia, vol. 95, No. 6, Dec. 2002, pp. 1686-1690; Database Biosis ponliun[ Biosciences Information Service, Philadelphia, PA.
Charalambous, et al., Comparison Of Peripheral And Central Venous Pressures In Critically Ill Patients, Anaesth Intensive Care. 2003; 31:34-9.

(56) References Cited

OTHER PUBLICATIONS

Nilsson, Macrocirculation Is Not The Sole Determinant Of Respiratory Induced Variations In The Reflection Mode, Physiological Measurement [0967-3334] 2003; 24:935.

Tobias, et al., Measurement Of Central Venous Pressure From A Peripheral Vein In Infants And Children, Pediatr Emerg Care. 2003; 19:428-30.

Bouchard, et al., Poor Correlation Between Hemodynamic And Echocardiographic Indexes Of Left Ventricular Performance In The Operating Room and Intensive Care Unit, Crit Care Med, 2004; 32(3): p. 644-8.

Yamakage, et al., Can Variation Of Pulse Amplitude Value Measured By A Pulse Oximeter Predict Intravascular Volume?, Anesthesiology 2004 abstracts.

Weingarten, et al., Peripheral Venous Pressure As A Measure Of Venous Compliance During Pheochromocytoma Resection, Anesth Analg. 2004; 99:1035-7, Table Of Contents.

Milhoan, et al., Upper Extremity Peripheral Venous Pressure Measurements Accurately Reflect Pulmonary Artery Pressures In Patients With Cavopulmonary Or Fontan Connections, Pediatr Cardiol. 2004 ;25:17-9.

Desjardins, et al., Can Peripheral Venous Pressure Be Interchangeable With Central Venous Pressure In Patients Undergoing Cardiac Surgery?, Intensive Care Med. 2004; 30:627-32.

Weingarten, T. N., et al., "Peripheral Venous Pressure As A Measure of Venous Compliance During Pheochromocytoma Resection," Anesthesia & Analgesia, 99: 1035-7, 2004.

Shelley, Kirk, H., M.D., Ph.D., et al., "The Effect of Venous Pulsation on the Forehead Pulse Oximeter Wave Form As A Possible Source of Error in $Spo_2$ Calculation," Anesthesia & Analgesia., 100: 743-7, 2005.

Hadimioglu, et al., Correlation Of Peripheral Venous Pressure And Central Venous Pressure In Kidney Recipients, Transplant Proc. 2006; 38:440-2.

Hoftman, et al., Peripheral Venous Pressure As A Predictor Of Central Venous Pressure During Orthotopic Liver Transplantation, J Clin Anesth. 2006; 18:251-5.

Mohrman, Cardiovascular Physiology. 6th ed. New York: McGraw-Hill Medical; 2006.

Shelley, Kirk H., M,D., Ph.D., et al., "The Use of Joint Time Frequency Analysis to Quantify the Effect of Ventilation of the Pulse Oximeter Waveform," Journal of Clinical Monitoring and Computing, 7 pages, 2006.

Awad, A. A. M.D., et al., "Analysis of the Ear Pulse Oximeter Waveform," Journal of Clinical Monitoring and Computing, 20: 175-184, 2006.

Shelley, Kirk, H., M.D., Ph.D., et al., "What Is the Best Site for Measuring the Effect of Ventilation of the Pulse Oximeter Waveform?", Technology, Computing, and Simulation, vol. 103, No. 2, Aug. 2006.

Choi, et al., Can Peripheral Venous Pressure Be An Alternative To Central Venous Pressure During Right Hepatectomy In Living Donors?, Liver Transpl. 2007; 13:1414-21.

Gesquiere, Michael J., M.D., et al., "Impact of Withdrawal of 450 ML of Blood on Respiration-Induced Oscillations of the Ear Plethysmographic Waveform," Journal of Clinical Monitoring and Computing, 21: 277-282, 2007.

Shelley, Kirk H., M.D., Ph.D., "Photoplethysmography: Beyond the Calculation of Arterial Oxygen Saturation and Heart Rate," Anesthesia & Analgesia, vol. 105, No. 8, Aug. 2007.

Awad, A. A,, M.D., et al., "The Relationship Between the Photoplethysmographic Waveform and Systemic Vascular Resistance," Journal of Clinical Monitoring and Computing, 8 pages, 2007.

Lu, Sheng, Ph.D., et al., "Can Photoplethysmography Variability Serve as an Alternative Approach to Obtain Heart Rate Variability Information?," Journal of Clinical Monitoring and Computing, 7 pages, 2007.

Baty, et al., Measurement Of Central Venous Pressure From A Peripheral Intravenous Catheter Following Cardiopulmonary Bypass In Infants And Children With Congenital Heart Disease, J Intensive Care Med. 2008; 23:136-42.

Jablonka, D. H., M.D., et al., "Comparing the Effect of Arginine Vasopressin on Ear and Finger Photoplethysmography," Journal of Clinical Anesthesia, 4 pages, 2008.

Supplementary European Search Report dated Jun. 16, 2009.

PCT International Search Report and Written Opinion dated Apr. 13, 2010.

Bland, J.M. et al., *A note on the use of the intraclass correlation coefficient in the evaluation of agreement between two methods of measurement*, Computers in Biology and Medicine, 20: 337-40 (1990).

Marik, P.E., *The systolic blood pressure variation as an indicator of pulmonary capillary wedge pressure in ventilated patients*, Anaesthesia & Intensive Care, 21: 405-8 (1993).

Gunther, et al., *Wavelet Analysis of Arterial Pressure and Blood Velocity Pulsations in the Aorta of Anesthetized Dogs*, Biol. Res. 26: pp. 391-396, 1993.

Coriat, P. et al., *A comparison of systolic blood pressure variations and echocardiographic estimates of end-diastolic left ventricular size in patients after aortic surgery*, Anesthesia & Analgesia, 78: 46-53 (1994).

Fearnley, Pulse Oximetry, Practical Procedures, Issue 5, 1995, Article 2.

Rooke, G.A. et al., *The effect of graded hemorrhage and intravascular volume replacement on systolic pressure variation in humans during mechanical and spontaneous ventilation*, Anesthesia & Analgesia, 80: 925-32 (1995).

Murray, et al., "The Peripheral Pulse Wave: Information Overlooked" Journal of Clinical Monitoring, vol. 12, No. 5, 1996, pp. 365-377.

Rusch, T.L. et al., *Signal processing methods for pulse oximetry*, Computers in Biology and Medicine, 26: 143-59 (1996).

Bernardi et al., Synchronous and Baroreceptor-Sensitive Oscillations in Skin Microcirculation Evidence for Central Autonomical Control, Am. J. Physiol. 1997, 273:H1867-1878.

Varanini et al., Spectral Analysis of Cardiovascular Time Series by the S-Transform, Computers in Cardiology 1997 Lund, Sweden Sep. 7-10, 1997, New York, NY, US, pp. 383-386.

Jimenez, et al., Continuous Wavelet Transform of Aortic Pressure Oscillations in Anesthetized Dogs: Effect of 45 deg. Tilting, Biol. Res. 30: pp. 53-64, 1997.

Jimenez et al., Time-Frequency Analysis of Arterial Pressure Oscillations in Anesthetized Dogs: Effects of Standarized Hemorrhages, Shock (Philadelphia); Injury, Inflammation and Sepsis: Laboratory and Clinical Approaches, Lippincott Williams & Wilkins, US, vol. 15, No. 2, Feb. 1, 2001, pp. 143-150.

Podgoreanu et al., Synchronous Rhythmical Vasomotion in the Human Cuatneous Microvasculature During Nonpulsatile Cardiopulmonary Bypass, Anesthesiology, 97:1110-1116, 2002.

Golparvar, et al., *Evaluating the Relationship Between Arterial Blood Pressure Changes and Indices of Pulse Oximetric Plethysmography*, Anesthesia and Analgesia, vol. 95, No. 6, Dec. 2002, pp. 1686-1690; Database Biosis [online] Biosciences Information Service, Philadelphia, PA.

Shamir et al., Plethysmographic Waveform Variation as an Indicator to Hypovolemia, Anesthesia Analgesia, 97:602-603,2003.

Wendelken, et al., A Preliminary Study of Respiratory Variations in the Photoplethysmogram During Lower Body Negative Pressure, Institute for Security Technology Studies, Darmouth College, Hanover, HH, pp. 391-395, 2006.

European Search Report dated Jan. 24, 2012.

PCT International Search Report for PCT/US2004/00027, Form PCT/USA/210, pp. 1-2.

\* cited by examiner

VOLUME STATUS MONITOR: PERIPHERAL VENOUS PRESSURE, HYPERVOLEMIA AND COHERENCE ANALYSIS

CROSS-REFERENCE TO RELATED APPLICATIONS

The present application claims the benefit of two Provisional Patent Applications Ser. Nos. 61/106,257, filed Oct. 17, 2008 and entitled "Method of Assessing Blood Volume Using Ventilation-Induced Variation VIV in Peripheral Venous Pressure PVP Alone In Comparison to VIV in Arterial Pressure and Plethysmographic Volume Tracings," and Ser. No. 61/159,621, filed Mar. 12, 2009 and entitled "Volume Status Monitor Hypervolemia and Coherence Analysis." The entire content of the foregoing provisional patent applications are incorporated herein by reference.

BACKGROUND

1. Technical Field

The present disclosure relates to systems and methods for analyzing flow waveforms in the peripheral vasculature, e.g., for assessing changes in blood volume.

2. Background Art

The present disclosure expands on and extends the teachings of U.S. Patent Publication No. 2007/0032732 to Shelley et al., entitled "Method of Assessing Blood Volume using Photoelectric Plethysmography" (referred to herein as the "Shelley Publication"). Accordingly, the foregoing patent publication is incorporated herein in its entirety.

Traditionally, invasive monitoring has been required to detect decreases in intravascular volume. In recent years, however, intraoperative monitoring has been moving towards minimally-invasive or non-invasive techniques. This shift has been attributed to various considerations, including procedure time, cost, and known risks which for traditionally invasive techniques may include carotid artery puncture, arrhythmia, pneumothorax, and infection. Indeed, there is growing evidence that invasive monitors of volume status, such as the pulmonary artery catheter (PAC), may be a source of unacceptably frequent complications. Dalen J & Bone R, *Is it time to pull the pulmonary artery catheter?*, JAMA 1996; 276: 916-14; Connors A, Speroff T & Dawson N, *The effectiveness of right heart catheterization in the initial care of critically ill patients*, JAMA 1996; 276:889-97. Thus, insertion of such monitors for the sole purpose of monitoring volume status often is withheld so as to avoid iatrogenic complications as well as to reduce costs and delays. In addition the accuracy and clinical usefulness of these monitors have been questioned. See e.g., Bouchard, M. J., et al., *Poor correlation between hemodynamic and echocardiographic indexes of left ventricular performance in the operating room and intensive care unit*. Crit. Care Med, 2004. 32(3): p. 644-8. The potential loss of this and other important monitors from routine perioperative care necessitates the search for another means of monitoring a patient's blood volume status. Hence, there is a need for minimally-invasive or non-invasive alternative systems and methods for assessing a patient's volume status, particularly in emergency, preoperative, and intensive care settings. Ideally, such systems and methods should be able to detect decreases in blood before major complications develop (e.g., before decreased blood pressure).

The Plethysmographic Waveform:

To meet these needs, investigators have been pursuing methods for assessing blood volume based on cardiovascular waveforms which are detectable in the peripheral vasculature. One such waveform is the plethysmographic (PG) waveform as may be obtained, e.g., via a pulse oximeter. In the process of determining oxygen saturation, a pulse oximeter inherently functions as a photoplethysmograph, measuring minute changes in the blood volume of a vascular bed (e.g., finger, ear or forehead). Thus, while the predominant application of a pulse oximeter has been calculating oxygen saturation of Hb, it is noted that the raw PG waveform is rich in information relevant to the physiology of the patient. Indeed, the PG waveform contains a complex mixture of the influences of arterial, venous, autonomic and respiratory systems on the peripheral circulation. It is important to understand, however, that the typical pulse oximeter waveform presented to the clinician is a highly filtered and processed specter of the original PG signal. Indeed, it is normal practice for equipment manufacturers to use both auto-centering and auto-gain routines on the displayed waveforms so as to minimize variations in the displayed signal. While such signal processing may be beneficial to the determination of oxygen saturation, it often comes at the expense of valuable physiological data. Thus, due to a general lack of access to the raw PG waveform and the overriding clinical importance of monitoring oxygen saturation, various other potential uses for the PG waveform have been largely neglected.

It is disclosed in the literature that a PG can be used to non-invasively measure minute changes in light absorption of living tissue. See, e.g., Hertzman, A B, "The Blood Supply of Various Skin Areas as Estimated By the Photoelectric Plethysmograph," Am. J. Physiol. 124: 328-340 (1938). Rhythmic fluctuations in this signal are normally attributed to the cardiac pulse bringing more blood into the region being analyzed (e.g., finger, ear or forehead). This fluctuation of the PG signal is commonly referred to as the pulsatile or AC (arterial) component. The amplitude of the AC component can be modulated by a variety of factors, including cardiac stroke volume and vascular tone. In addition to the pulsatile component of the PG signal, there is a nonpulsatile (or weakly pulsatile) component of the PG signal commonly referred to as the DC component. The DC component is most commonly attributed to changes in light absorption by nonpulsatile tissue, such as fat, bone, muscle and venous blood. Thus, the DC component has been correlated to changes in venous blood volume (see, e.g., paragraph [0059] of the Shelley publication).

Methods for extracting and analyzing the AC and DC components of the PG signal are provided in the Shelley publication. The ability to independently monitor changes in venous and arterial blood volume has many clinical applications. For example, changes in venous and arterial blood volume may be indicative of Hypovolemia, e.g., due to bleeding, dehydration, etc. Decreased blood volume due to bleeding is, typically, characterized by an initial period of venous loss during which the cardiac output remains unaffected. With continued blood loss, decreased venous return eventually affects cardiac output (corresponding to arterial blood volume).

It is again noted, however, since the main purpose of the pulse oximeter is determination of arterial oxygen saturation, most pulse oximeters filter out the venous (DC) component and normalize the arterial (AC) component to facilitate visualization of the signal. In addition, pulse oximeters are most commonly used on the finger, a region rich in sympathetic innervation that often reflects local (as opposed to systemic) alterations in vascular tone and volume status. See, e.g., Yamakage M, Itoh T, Iwasaki S, Jeong S-W, Namiki A, *Can variation of pulse amplitude value measured by a pulse oximeter predict intravascular volume?*, Anesthesiology 2004 abstracts; Dorlas J C, Nijiboer J A, *Photo-electric*

*plythysmography as a monitoring device in anaesthesia. Application and interpretations*, BR J Anaethesia 1999 82(2): 178-81; A245, H188, H236.

Peripheral Venous Pressure:

A further largely unexplored source of clinical information is pressure transduction of the standard intravenous line. A vast majority of hospitalized patients have a peripheral venous line. It is placed to allow fluids and medications to be given directly into the circulatory system. Until recently, the venous system's contribution to the circulatory system has been incorrectly identified as being insignificant. Indeed, veins do more than merely conduct blood to the heart; veins play a critical role in cardiovascular homeostasis. Thus, considering the ease of measurement from a peripheral intravenous catheter, further investigation of the utility and limitations of such a minimally invasive and inexpensive monitoring device is warranted.

Folkow, in the 1960s, studied the characteristics of veins and noted the huge disparity which existed in the literature concerning the amount of information on the arterial vs. the venous sides of the circulation. Folkow B, Mellander S., *Veins and Venous Tone*, Am Heart J. 1964; 68:397-408. Almost 50 years later, we have still not filled the gap. While arterial waveforms have been studied extensively, focus on the peripheral venous component has been scarce.

Controversy still exists concerning the role of peripheral veins and their contribution to the central volume in face of blood loss. Many studies in the late 1990s and early 2000s have shown a consistent correlation between peripheral venous pressure (PVP) and central venous pressure (CVP). See, e.g., Weingarten T N, Sprung J, Munis J R., *Peripheral venous pressure as a measure of venous compliance during pheochromocytoma resection*, Anesth Analg. 2004; 99:1035-7, table of contents; and Charalambous C, Barker T A, Zipitis C S, Siddique I, Swindell R, Jackson R, et al., *Comparison of peripheral and central venous pressures in critically Ill patients*, Anaesth Intensive Care. 2003; 31:34-9. While CVP waveforms characteristically show a-, c-, and v-waves, PVP waveforms often appear as a more dampened sinusoidal pattern. Munis et al. reported mean PVP values of 13 mm Hg, CVP values of 10 mm Hg, with a PVP-CVP difference of 3 mm Hg (see Munis J. R., Bhatia et al., *Peripheral venous pressure as hemodynamic variable in neurosurgical patients*, Anesth Analg 2001; 91(1): 172-9). Amar et al. observed mean PVP values of 9 mm Hg and a mean CVP value of 8 mm Hg in 100 intraoperative patients (see Amar D, Melendez J A, Zhang H, Dobres C, Leung D H, Padilla R E, *Correlation of peripheral venous pressure and central venous pressure in surgical patients*, J Cardiothorac Vasc Anesth. 2001; 15:40-3). Hadimioglu et al. came to the same conclusions in patients undergoing kidney transplant (see Hadimioglu N, Ertug Z, Yegin A, Sanli S, Gurkan A, Demirbas A, *Correlation of peripheral venous pressure and central venous pressure in kidney recipients*, Transplant Proc. 2006; 38:440-2). Baty et al studied 29 infants and children post cardiopulmonary bypass. The difference between peripheral venous pressure and central venous pressure in these patients was 11±3 mm Hg. No clinically significant variation in the accuracy of the technique was noted based on the actual CVP value, size of the PIV, its location, or the patient's weight (see Baty L, Russo P, Tobias J D, *Measurement of central venous pressure from a peripheral intravenous catheter following cardiopulmonary bypass in infants and children with congenital heart disease*, J Intensive Care Med. 2008; 23:136-42).

Other authors have done similar assessments in patients undergoing right hepatectomy. In Choi et al., a central venous catheter was placed through the right internal jugular vein and a peripheral venous catheter was inserted at the antecubital fossa in the right arm. A total of 1,430 simultaneous measurements of CVP and PVP were recorded. Choi concluded the difference between PVP and CVP was within clinically acceptable agreement and the degree of difference tended to remain relatively constant throughout the right hepatectomy in living donors. (See Choi S J, Gwak M S, Ko J S, Kim G S, Kim T H, Ahn H, et al., *Can peripheral venous pressure be an alternative to central venous pressure during right hepatectomy in living donors?*, Liver Transpl. 2007; 13:1414-21). Hoftman et al. studied the correlation of both variables in patients undergoing liver transplant. The nature of the liver transplant surgery allowed the authors to test the durability of the PVP/CVP correlation during extreme derangements of physiology, including IVC crossclamp, brisk hemorrhage, and reperfusion of the donor graft. One unexpected finding, not previously reported in other studies, was the much weaker PVP/CVP correlation at low filling pressures. It was suggested that at low filling pressures, peripheral veins intermittently collapse, interrupting their continuity with the central circulation and thus leading to PVP/CVP divergence. (See Holtman N, Braunfeld M, Holtman G, Mahajan A., *Peripheral venous pressure as a predictor of central venous pressure during orthotopic liver transplantation*, J Clin Anesth. 2006; 18:251-5).

According to Munis et al. (2001), PVP may be used as an indirect measure of venous volume since pressure is related to volume/compliance. Alternatively, it was reported that fluctuations of PVP are highly influenced by changes in vascular tone. Thus, measurements of volume status using PVP may be distorted by local changes in vascular tone. Vincent at al. documented that hand vein compliance decreases in responses to the alpha-agonist phenylephrine. Vincent J, et al., *Cascular reactivity to phenylephrine and angiotensin II: comparison of direct venous and systemic vascular responses*, Clin Pharmacol Ther 1992; 51:68-75.

Moreover, the relationship of peripheral venous pressure and central venous pressure differs among patients. For example, the offset in Munis' study averaged 3.0 mmHg, ranging from 0.5 to 8.9 mmHg over 15 subjects. Similarly, Pederson et al. reported a mean gradient of 2.6 cm $H_2O$ and a range of 0.7 to 5.8 cm $H_2O$ between the antecubital vein and right atrium. Hence, without a baseline comparison to CVP (which requires invasive insertion of a central venous catheter), it is difficult to determine the accuracy of PVP measurements.

Generally, while there have been attempts to relate PVP to CVP (see, e.g., Eustace B R., *A comparison between peripheral and central venous pressure monitoring under clinical conditions*, Injury 1970; 2(1):12-18; Choi S J, Gwak M S, Ko J S, Kim G S, Kim T H, Ahn H, et al., *Can peripheral venous pressure be an alternative to central venous pressure during right hepatectomy in living donors?*, Liver Transpl. 2007; 13:1414-21; Holtman N, Braunfeld M, Holtman G, Mahajan A., *Peripheral venous pressure as a predictor of central venous pressure during orthotopic liver transplantation*, J Clin Anesth. 2006; 18:251-5; Milhoan K A, Levy D J, Shields N, Rothman A., *Upper extremity peripheral venous pressure measurements accurately reflect pulmonary artery pressures in patients with cavopulmonary or Fontan connections*, Pediatr Cardiol. 2004; 25:17-9.; Tobias J D, Johnson J O., *Measurement of central venous pressure from a peripheral vein in infants and children*, Pediatr Emerg Care. 2003; 19:428-30; and Desjardins R, Denault A Y, Belisle S, Carrier M, Babin D, Levesque S, et al., *Can peripheral venous pressure be interchangeable with central venous pressure in patients undergoing cardiac surgery?*, Intensive Care Med. 2004; 30:627-

32), very little effort has been made to characterize the PVP waveform as an independent entity.

In the past, a number of investigators have advanced the concept that a small change in venous capacity, induced by venous constriction or relaxation, should markedly alter the cardiac output. See, e.g., Bartelstone H J., *Role of the veins in venous return*, Circ Res. 1960; 8:1059-76. In a delicately designed experiment involving dogs, Bartelstone was able to divide the venous system into two major components: (1) the central venous conduit, holding approximately 18% of the total blood volume and including the inferior Vena Cava (IVC) and the large vein continuations thereof, and (2) the reactive venous reservoir, containing approximately 45% of the total blood volume and including the veins between the capillaries and the central venous conduit. Bartelstone was also able to demonstrate that there exists an intravenous gradient which facilitates the movement from the reactive venous reservoir to the central venous conduit. Bartelstone further displayed that sympathetic stimulation had no significant impact on the central venous conduit, despite a dynamic impact on the reactive venous reservoir.

Venous Compliance:

Rothe in the 1990s effectively tackled the issue of compliance in the venous compartment. Thus, Rothe illustrated the concept of Mean Circulatory Filling Pressure (PMCF) described first by Guyton. He defined PMCF as mean vascular pressure that exists after circulatory arrest leading to redistribution of blood, so that all pressures are the same throughout the system. PMCF is thus related to the fullness of the circulatory system. This pressure has been measured and found to be close to 7 mm of Hg. This is clearly less than capillary pressure, but it is greater than the venous pressure at the atrio-caval junction under normal conditions. See Rothe C F, *Mean circulatory filling pressure: its meaning and measurement*, J Appl Physiol. 1993; 74:499-509.

As is evident from FIG. 1P, there is a huge contrast between venous and arterial compliance. The enormous compliance of veins allows for huge shifts of circulating volume in and out of the venous compartment. Peripheral venous constriction, as evidenced by the dashed line, tends to increase venous pressure and shift blood out of the venous compartment. Mohrman D, *Cardiovascular Physiology*. 6th ed. New York: McGraw-Hill Medical; 2006.

Two primary factors are known to affect peripheral venous tone: (1) blood volume within the veins: because the veins are so much more compliant, changes in circulating blood volume produce larger changes in the volume of blood in the veins than in any other vascular segment. Tyberg J V, *How changes in venous capacitance modulate cardiac output*, Pflugers Arch. 2002; 445:10-7; and (2) sympathetic venous activity. In addition, an increase in any force compressing veins from the outside has the same effect on the pressure inside veins as an increase in venous tone. Thus, such things as muscle exercise and wearing elastic stockings tend to elevate peripheral venous pressure.

The relationship between central venous pressure and venous return is known as the Venous Return Curve (see FIG. 2P). When venous tone changes, so does the central venous pressure. For example, whenever peripheral venous pressure is elevated by increases in blood volume or by sympathetic stimulation, the venous function curve shifts upward and to the right.

Mohrman D 2006. This is believed to be caused by a decrease in venous capacitance which raises the mean circulatory pressure, which in turn tends to increase all intravascular pressures, and thus increases the preload of the heart. Id.

In the year 1955, Guyton, a man known for his valuable contributions to the field of physiology, explained the relationship between venous compliance and cardiac output. He used Starling's law for the determination of cardiac output which he defined as the relationship between the cardiac output and right atrial pressure and called the "cardiac response curve". Guyton A C, *Determination of cardiac output by equating venous return curves with cardiac response curves*, Physiol Rev. 1955; 35:123-9

FIG. 3P demonstrates that peripheral venous constriction increases cardiac output by raising central venous pressure and moving the heart's function upward along a fixed cardiac function curve. FIG. 3P also depicts the response of the vasculature to hemorrhage into progressive steps (i.e., A to B to C to D) which does not happen discretely in reality. The actual course of a patient's net response to hemorrhage would appear to follow nearly a straight line from point A to point D.

The behavior of peripheral veins of the forearm, in response to hemorrhage or sympathetic activity, is conflicting. While Zoller was able to demonstrate that the forearm veins show intense venoconstriction in the absence of changes in other hemodynamic parameters, other studies have proved that those limb veins have very little role to play in contributing to the central blood volume. Zoller R P, Mark A L, Abboud F M, Schmid P G, Heistad D D, *The role of low pressure baroreceptors in reflex vasoconstrictor responses in man*, J Clin Invest. 1972; 51:2967-72.

Ventilation-Induced Variation

It has been known for quite some time that ventilation, and especially positive pressure ventilation, can have a significant impact on the cardiovascular system. Cournand A, Modey H, Werko L & Richards D, *Physiological studies of the effect of intermittent positive pressure breathing on cardiac output in man*, Am J Physio 1948; 152:162-73; Morgan B, Crawford W & Guntheroth W, *The homodynamic effects of changes in blood volume during intermittent positive-pressure ventilation*, Anesthesiology 1969; 30:297-305. The first formal studies of the effect of ventilator induced changes on arterial pressure were done in the early 1980's. Coyle J, Teplick R, Long M & Davison J. *Respiratory variations in systemic arterial pressure as an indicator of volume status*, Anesthesiology 1983; 59:A53; Jardin F, Fareot J, Gueret P et al., *Cyclic changes in arterial pulse during respiratory support*, Circulation 1983; 68:266-74. This recognition was soon followed by the intensive investigations of Azriel Perel who coined the term "systolic pressure variation" to describe this phenomenon. Along with various co-investigators, his research has encompassed over twenty articles and abstracts on the topic. From this significant body of work, based on both animal and human data, a number of conclusions have been drawn.

It has been shown that the responses of peripheral waveforms to respiration can be used as an indicator of hypovolemia. More specifically, arterial pressure waveforms in the periphery (e.g., radial artery) demonstrate increased systolic pressure variations in the context of hypovolemia (as a result of ventilation affecting venous return to the heart and hence affecting left ventricular stroke volume). The degree of systolic pressure variation is a sensitive indicator of hypovolemia. Perel A, Pizov R & Cotev S, *Systolic blood variation is a sensitive indicator of hypovolemia in ventilated dogs subjected to graded hemorrhage*, Anesthesiology 1987; 67:498-502. This variation is significantly better than heart rate, central venous pressure and mean systemic blood pressure in predicting the degree of hemorrhage which has occurred. Perel A, Pizov R & Cotev S, *Systolic blood pressure variation is a sensitive indicator of hypovolemia in ventilated*

*dogs subjected to graded hemorrhage*, Anesthesiology 1987; 67:498-502; Pizov R, Ya'ari Y & Perel A, *Systolic pressure variation is greater during hemorrhage than during sodium nitroprusside-induced hypotension in ventilated dogs*, Anesthesia & Analgesia 1988; 67:170-4. Chest wall compliance and tidal volume can influence systolic pressure variation. Szold A, Pizov R, Segal E & Perel A, *The effect of tidal volume and intravascular volume state on systolic pressure variation in ventilated dogs*, Intensive Care Medicine 1989; 15:368-71. Changes in systolic pressure variation correspond closely to changes in cardiac output. Ornstein E, Eidelman L, Drenger B et al., *Systolic pressure variation predicts the response to acute blood loss*, Journal of Clinical Anesthesia 1998; 10:137-40; Pizov R, Segal E, Kaplan L et al., *The use of systolic pressure variation in hemodynamic monitoring during deliberate hypotension in spine surgery*, Journal of Clinical Anesthesia 1990; 2:96-100.

Systolic pressure variation can be divided into two distinct components; Δup, which reflects an inspiratory augmentation of the cardiac output, and Δdown, which reflects a reduction in cardiac output due to a decrease in venous return. Perel A, *Cardiovascular assessment by pressure waveform analysis*, ASA Annual Refresher Course Lecture 1991:264. The unique value in systolic pressure variation lies in its ability to reflect the volume responsiveness of the left ventricle. Perel A, *Cardiovascular assessment by pressure waveform analysis*, ASA Annual Refresher Course Lecture 1991:264. In recent years, with the increased availability of the pulse oximeter waveform, similar observations have been made with this monitoring system. Partridge B L, *Use of pulse oximetry as a noninvasive indicator of intravascular volume status*, Journal of Clinical Monitoring 1987; 3:263-8; Lherm T, Chevalier T, Troche G et al., *Correlation between plethysmography curve variation (dpleth) and pulmonary capillary wedge pressure (pcup) in mechanically ventilated patients*, British Journal of Anesthesia 1995; Suppl. 1:41; Shamir M, Eidelman L A et al., *Pulse oximetry plethysmographic waveform during changes in blood volume*, British Journal Of Anaesthesia 82(2): 178-81 (1999).

To date, however, there has been remarkably little work done to document or quantify the phenomenon of systolic pressure variation. Limitations of the aforementioned include, inter alia, reliance on positive pressure and mechanical ventilation; and the requirement of ventilator maneuvers, such as periods of apnea.

As for detecting systolic pressure variation, it is noted that changes in intrathoracic pressure during ventilation causes variations in the PG signal. Fluctuations in the PG signal due to respiration/ventilation can be detected. See, e.g., Johansson A & Oberg P A, "Estimation of respiratory volumes from the photoplethysmographic sit. Parti: Experimental results," Medical and Biological Engineering and Computing 37(1): 42-7 (1999). Respiratory-induced fluctuations have been used in the past in an attempt to estimate the degree of relative blood volume of patients undergoing surgery. See, e.g., Partridge B L, "Use of pulse oximetry as a noninvasive indicator of intravascular volume status," Journal of Clinical Monitoring 3(4): 263-8 (1987); and Shamir M, Eidelman L A et al., "Pulse oximetry plethysmographic waveform during changes in blood volume," British Journal of Anaesthesia 82(2): 178-81 (1999).

In the Shelley publication, it was first noted that respiration/ventilation modulates both the AC and DC components of the PG signal. Thus, the Shelley publication discloses, inter alia, methods for monitoring blood volume by separating the impact of ventilation on the arterial and venous systems. The ability to mathematically separate the impact of ventilation on the arterial (pulsatile component) and venous (nonpulsatile component) systems allows one to independently assess changes in blood volume in two different regions of the vasculature (arterial and venous). Venous blood volume corresponds to end-diastolic volume (EDV) (also referred to as preload). EDV directly impacts the amount of blood available to the heart before each contraction. Arterial blood volume corresponds to cardiac stroke volume. Cardiac stroke volume may be calculated by subtracting end-systolic volume (ESV) from EDV. Cardiac output is determined as cardiac stroke volume multiplied by heart rate.

As noted in the Shelley publication, the degree of respiratory-induced fluctuation of the DC component of the PG signal corresponds to venous blood volume. Thus, by monitoring respiratory-induced fluctuations of the DC component one can detect and counter blood loss (e.g., hypovolemia) prior to cardiac output being affected. Alternatively, one can detect and counter over fluidization (e.g., hypervolemia). Similarly, as noted in the Shelley publication, the degree of respiratory-induced fluctuation of the AC component of the PG signal corresponds to arterial volume. Thus, by monitoring respiratory-induced fluctuations of the AC component, one can detect the severity of blood loss (i.e., whether blood loss is severe enough to compromise cardiac function).

An alternate method suggested by the Shelley publication for assessing changes in blood volume involves harmonic analysis, e.g., Fourier analysis, of the PG waveform. Harmonic analysis allows for the extraction of underlying signals that contribute to a complex waveform. Similar methods have been used, e.g., to improve the accuracy of oxygen saturation measurements and to monitor tissue perfusion. See, e.g., Rusch T L, Sankar R & Scharf J E, "Signal processing methods for pulse oximetry," Computers in Biology and Medicine 1996; 26:143-59; and Stack B Jr., Futran N D, Shohet M N & Scharf J E, "Spectral analysis of photoplethysmograms from radial forearm free flaps," Laryngoscope 1998; 108:1329-33.

Harmonic analysis of the PG waveform, as disclosed in the Shelley publication, principally involves a short-time Fourier transform of the PG signal. In particular, the PG waveform may be converted to a numeric series of data points via analog to digital conversion, wherein the PG signal is sampled at a predetermined frequency, e.g., 50 Hz, over a given time period, e.g., 60-90 seconds. A Fourier transform may then be performed on the data set in the digital buffer (note that the sampled PG signal may also be multiplied by a windowing function, e.g., a Hamming window, to counter spectral leakage). The resultant data may further be expanded in logarithmic fashion, e.g., to account for the overwhelming signal strength of the cardiac frequencies relative to the ventilation frequencies. While the Shelley publication discloses joint time-frequency analysis, i.e., a spectrogram, as a preferred technique for viewing and analyzing spectral density estimation of the PG signal, the spectrum of the PG signal over a set period of time may be easily extrapolated therefrom.

According to the Shelley publication, harmonic analysis, such as described above, may be used to independently monitor changes in arterial and venous blood volume. For instance, an initial increase in signal strength for the respiratory signal is observed to be largely due to increased respiratory-induced fluctuation of the DC component of the PG signal indicative of venous loss (note that although an initial increase in the respiratory signal is reflective of venous loss, subsequent decreased cardiac output (e.g., resulting when decreased venous return affects the arterial system) may also contribute to changes in the respiratory signal). Similarly, changes in blood volume severe enough to affect the arterial system (cardiac output) were correlated to increased side-band modulation around the primary band of the cardiac signal. Thus, by monitoring variations in the respiratory signal one is able to detect changes in venous blood volume. Similarly, by monitoring side-band modulation of the cardiac signal one is able to detect changes in arterial blood volume.

Analysis of venous waveforms has indicated that, like arterial waveforms, they too exhibit respiratory variations and change in response to physiologic challenges. Brecher et al. examined the relationship of respiration on the intrathoracic (the central venous conduit) and extrathoracic veins (the reactive venous reservoir). Brecher et al. conducted experiments using both spontaneously breathing and mechanically ventilated dogs. Pressure recordings were obtained from the jugular vein, femoral artery, intrapleural space and right atrium. Brecher concluded the following for spontaneous breathing under normal volume status: (1) thoracic aspiration during inspiration causes increase in blood flow to the right atrium significantly due to the emptying of the extrathoracic veins into the central veins; (2) flow does not increase further once the collapsed state of extrathoracic veins has been reached; and (3) if inspiration is long and deep enough, flow may even drop slightly below its inspiratory maximum due to the exhaustion of the extrathoracic reservoir and the progressively increasing resistance offered by the partially collapsed extrathoracic veins. Brecher then studied the same relationship under conditions of hyper and hypovolemia and concluded that identical degrees of thoracic aspiration increase venous return only moderately in the hypovolemic state as compared to euvolemic state. Brecher further noted that the greater the hypovolemia, the shorter the duration and amount of the aspiratory flow augmentation and the earlier the onset of the collapsed stage. (See Brecher GA, Mixter G, Jr., *Effect of respiratory movements on superior cava flow under normal and abnormal conditions*, Am J. Physiol. 1953; 172:457-61).

Respiratory variations in the central venous waveform have been described before. The respiratory induced variation in central vein pressure also causes variations in arterial blood pressure (ABP), as described above, and in peripheral venous pressure (PVP). Valves in the venous system in the forearm may hinder hydrostatic continuity, implying that one single vein might not represent the entire venous system in the forearm. Whether the respiratory variation in PVP is a forward transmission of the change in arterial pressure or a backward transmission from the central venous system remains unclear. (see Nilsson, *Macrocirculation is not the sole determinant of respiratory induced variations in the reflection mode*, Physiological Measurement [0967-3334] 2003; 24:935).

SUMMARY

Systems and methods are provided according to the present disclosure for analyzing waveforms representative of the peripheral vasculature, e.g., for detecting changes in blood volume. In particular, the disclosed systems and methods relate, inter alia, to analyzing ventilation-induced variation (VIV, also referred to as respiration-induced variation) of waveforms representative of the peripheral vasculature.

Advantageously, the disclosed systems and methods may relate to analyzing VIV in peripheral venous pressure (PVP), e.g., such as may be detected via pressure transduction in a standard intravenous line. Thus, the VIV of PVP may be measured according to the present disclosure, wherein decreased VIV is indicative of decreased blood volume. In exemplary embodiments, VIV of PVP is compared to VIV in peripheral arterial pressure (PAP), e.g., wherein an index is calculated relating the VIV of PVP and the VIV in PAP. In further exemplary embodiments, VIV of PVP is compared to VIV in a PG signal, e.g., wherein an index is calculated relating the VIV of PVP to the VIV in the PG signal or in a component (e.g., arterial or venous) thereof.

In exemplary embodiments, such as involving spontaneous breathing, it may be necessary to account for changes in respiratory signal strength. Thus, systems and methods are also provided for assessing coherence between ventilation and VIV for a flow or pressure waveform. Specifically, coherence is evaluated according to exemplary embodiments of the present disclosure by comparing the waveform to a detected respiratory signal.

Further, systems and method are provided for distinguishing the impact of respiration on the PG signal during hypervolemia as compared to hypovolemia. Such systems and methods may advantageously be utilized to monitor fluid status during fluid replacement.

Additional features, functions and benefits of the disclosed systems and methods will be apparent from the description which follows, particularly when read in conjunction with the appended figures.

BRIEF DESCRIPTION OF THE DRAWINGS

To assist those of ordinary skill in the art in making and using the disclosed systems and methods, reference is made to the appended figures, wherein.

DESCRIPTION OF EXEMPLARY EMBODIMENT(S)

According to the present disclosure, advantageous systems and methods are provided for analyzing waveforms of the peripheral vasculature, e.g., peripheral venous pressure (PVP) a plethysmographic (PG) signal, etc. Advantageously, such waveforms may be used to detect changes in blood volume (e.g., a PG signal may be used to detect and distinguish between hypovolemia and hypervolemia as later provided herein). In particular, the present systems and methods relate to analyzing ventilation-induced variation (VIV, also referred to as respiration-induced variation) of waveforms in the peripheral vasculature. Thus, in exemplary embodiments, such as involving spontaneous breathing, it may be necessary to account for changes in respiratory signal strength. Specifically, coherence between ventilation and VIV for a flow or pressure waveform may be determined using spectral-domain analysis as later described herein. Indeed, mediation of respiration-induced variations in the spectral-domain overcomes/addresses many of the problems associated with detecting volume status in spontaneous breathing subjects.

Determining Volume Status from PVP:

In exemplary embodiments, PVP is analyzed. According to the present disclosure, PVP may be determined from an intravenous site. Indeed a vast majority of hospitalized patients have a peripheral venous catheter inserted as standard procedure. Analysis of PVP according to the present disclosure focuses on changes in VIV of PVP.

Lower body negative pressure (LBNP) is an experimental model that allows for the creation of reversible hypovolemic shock in spontaneously ventilating normal volunteers. It has been estimated that LBNP simulated the effect of an acute 1.5 to 2 liter blood loss. For purposes of demonstrating exemplary embodiments of the present systems and methods, the impact of LBNP on the PVP waveform was investigated with a specific focus on the impact of LBNP on VIV of PVP.

A description of the investigative procedures follows: Seven volunteers underwent a reversible LBNP protocol consisting of 3-minute windows at baseline, −30, −60, −75 and −90 mm Hg decompression and recovery. Subjects breathed at a metronomic rate of 12 breaths/min. LBNP termination occurred at onset of signs of cardiovascular collapse, e.g., systolic blood pressure (SBP)<80 mm Hg; Heart Rate (HR)=2× (wherein, x=base heart rate); pre-syncope symptoms; etc. EKG, blood pressure (Finapres), finger/forehead laser Doppler, finger/ear/forehead PG, and chest respiratory band were recorded at 200 Hz using a data acquisition system (PowerLab, ADInstruments). PVP was obtained from a 20 g catheter in an antecubital vein.

Figure 1P:
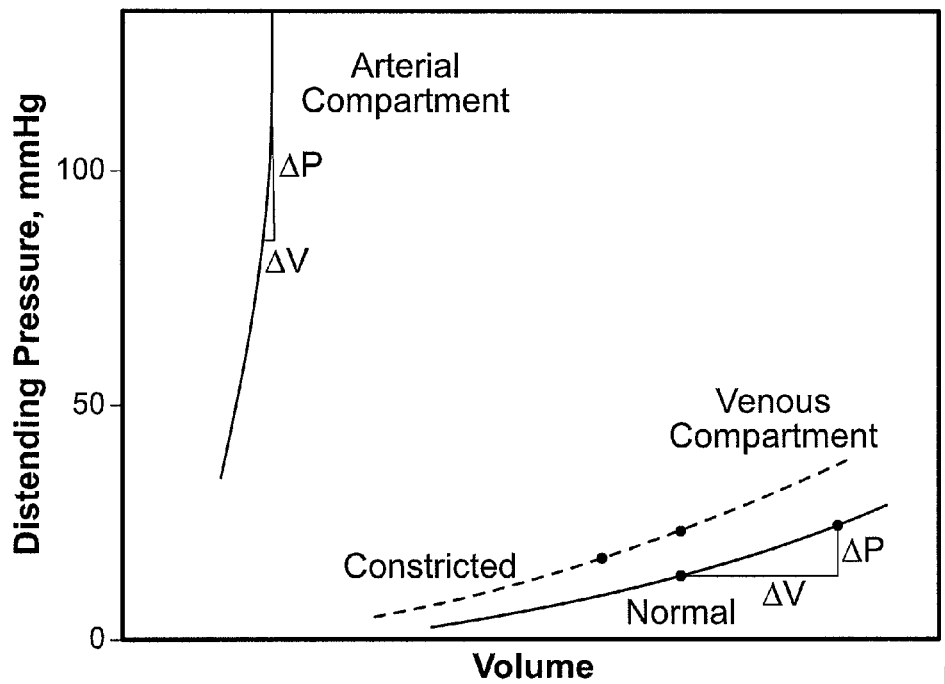
FIG. 1P (where the "P" designation references "prior art") depicts the relationship between volume and pressure both within the arterial and venous system.
Figure 2P:
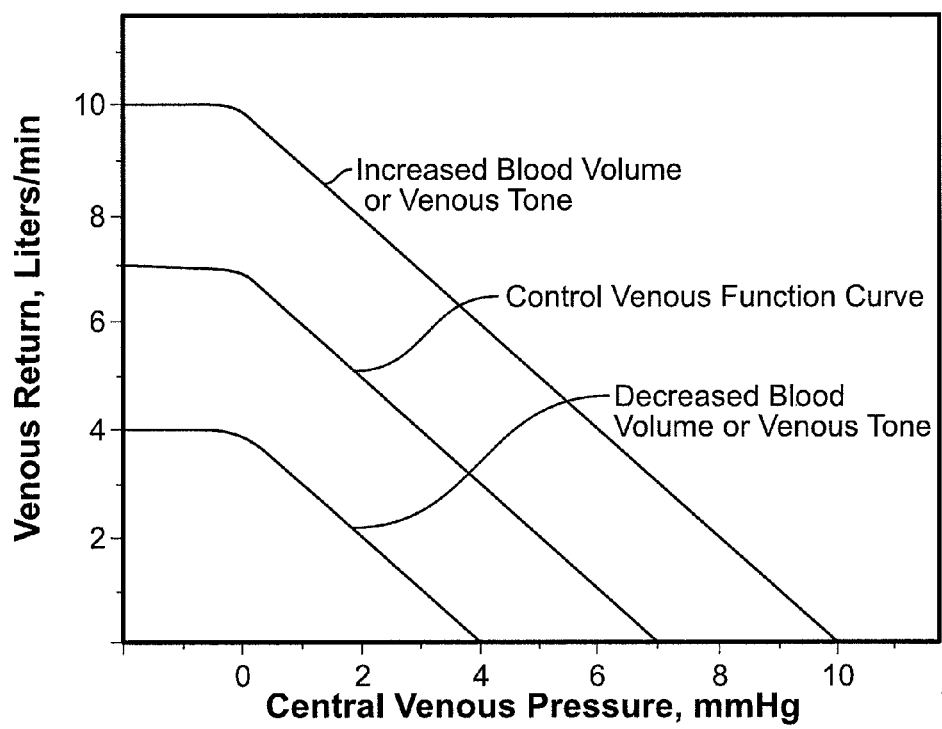
FIG. 2P depicts the relation between venous filling pressure and venous return.
Figure 3P:
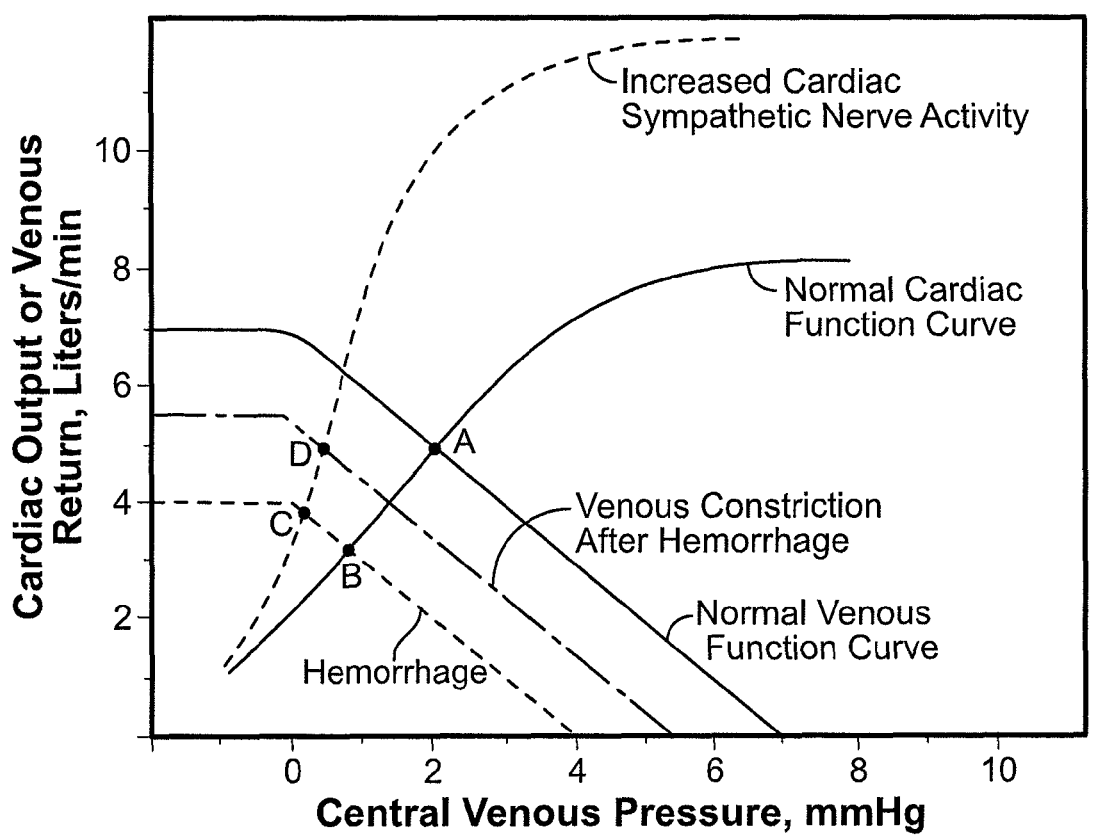
FIG. 3P depicts the relationship between the venous return curve and Starling cardiac output curve.
Figure 1:
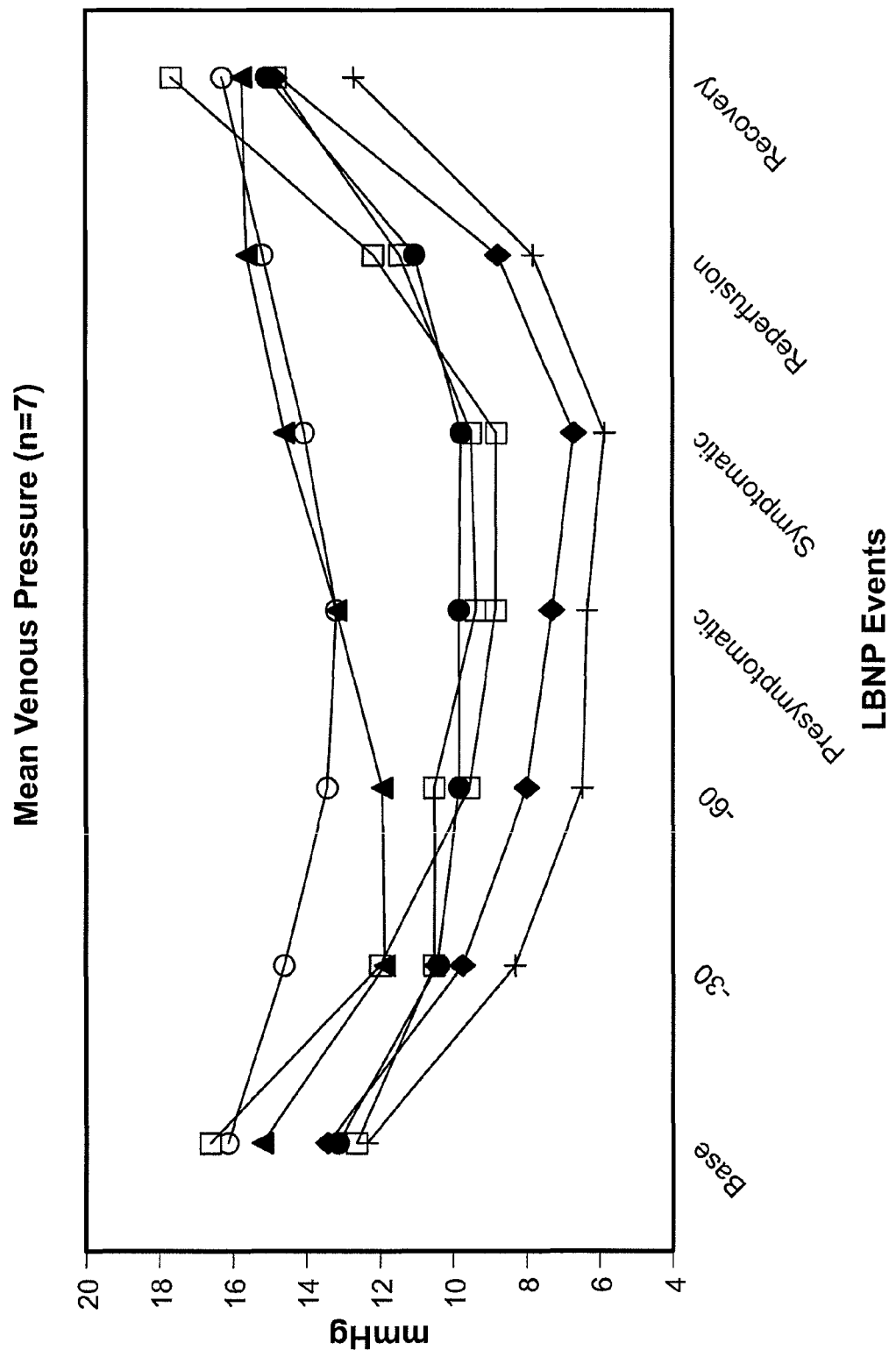
FIG. 1 depicts peripheral venous pressure (PVP) for seven (7) test subjects during lower body negative pressure (LBNP).

The results of the investigation are summarized as follows: On average the mean PVP declined by 32% (14.2 mmHg to 9.7 mmHG) from baseline to symptom development. FIG. 1 depicts PVP for each of the 7 test subjects as a function of LBNP stages. A two-tailed Wilcoxon analysis revealed the percentage decrease to be statistically significant.

Figure 2:
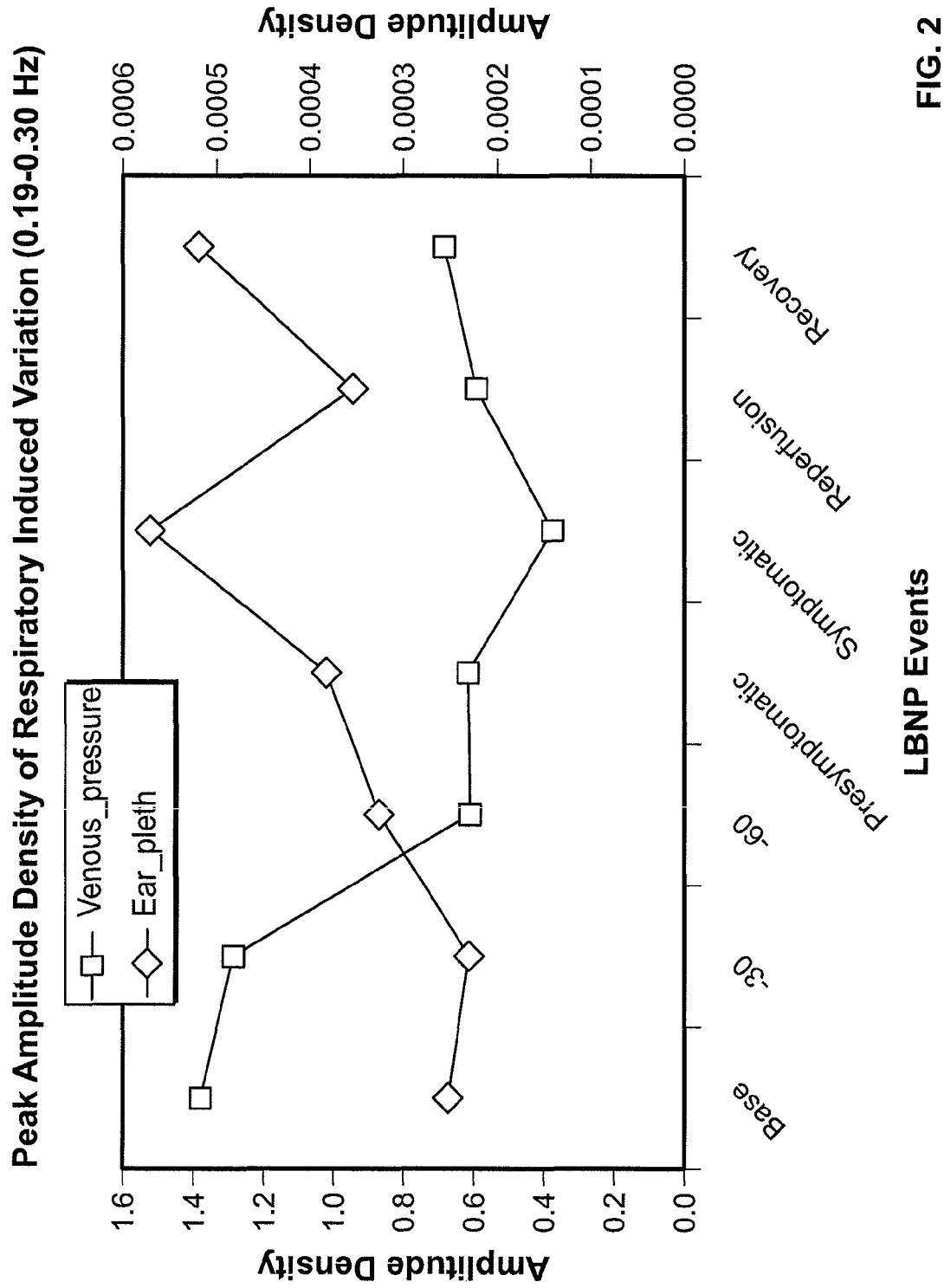
FIG. 2 depicts ventilation-induced variation (VIV) of PVP and VIV of a PG signal during LBNP as calculated using spectral analysis.

The degree of VIV of PVP was calculated using spectral analysis of the PVP waveform. Specifically, an amplitude density was monitored for the ventilation frequency. VIV of PVP showed a 70% reduction (amplitude density of 1.32 to 0.37 $mmHg^2/Hz$) as a result of LBNP. The degree of VIV in the PG signal was also calculated using spectral analysis. Note that VIV of arterial blood pressure may also be calculated, e.g., using an intra-arterial monitor. FIG. 2 depicts amplitude density for the ventilation frequency for both PVP and the PG signal as a function of the LBNP stages. Once again, this was found to be statistically significant using Wilcoxon analysis (p=0.043).

The decrease in mean PVP as a result of LBNP was predictable. The decrease in VIV of PVP was a more curious result. Presumably, PVP decreased as a result of sequestration of venous blood in the lower extremities during LBNP. This loss in effective venous volume thereby reduced the degree to which ventilation impacted on PVP (e.g., flat veins transmit pressure waves poorly).

The results further demonstrated a reciprocal relationship between arterial and venous VIV in response to hypovolemia (as simulated using LBNP) and hypervolemia. Specifically, VIV of the PG signal and systolic pressure variation were observed to increase as a result of decreased blood volume.

Figure 3:
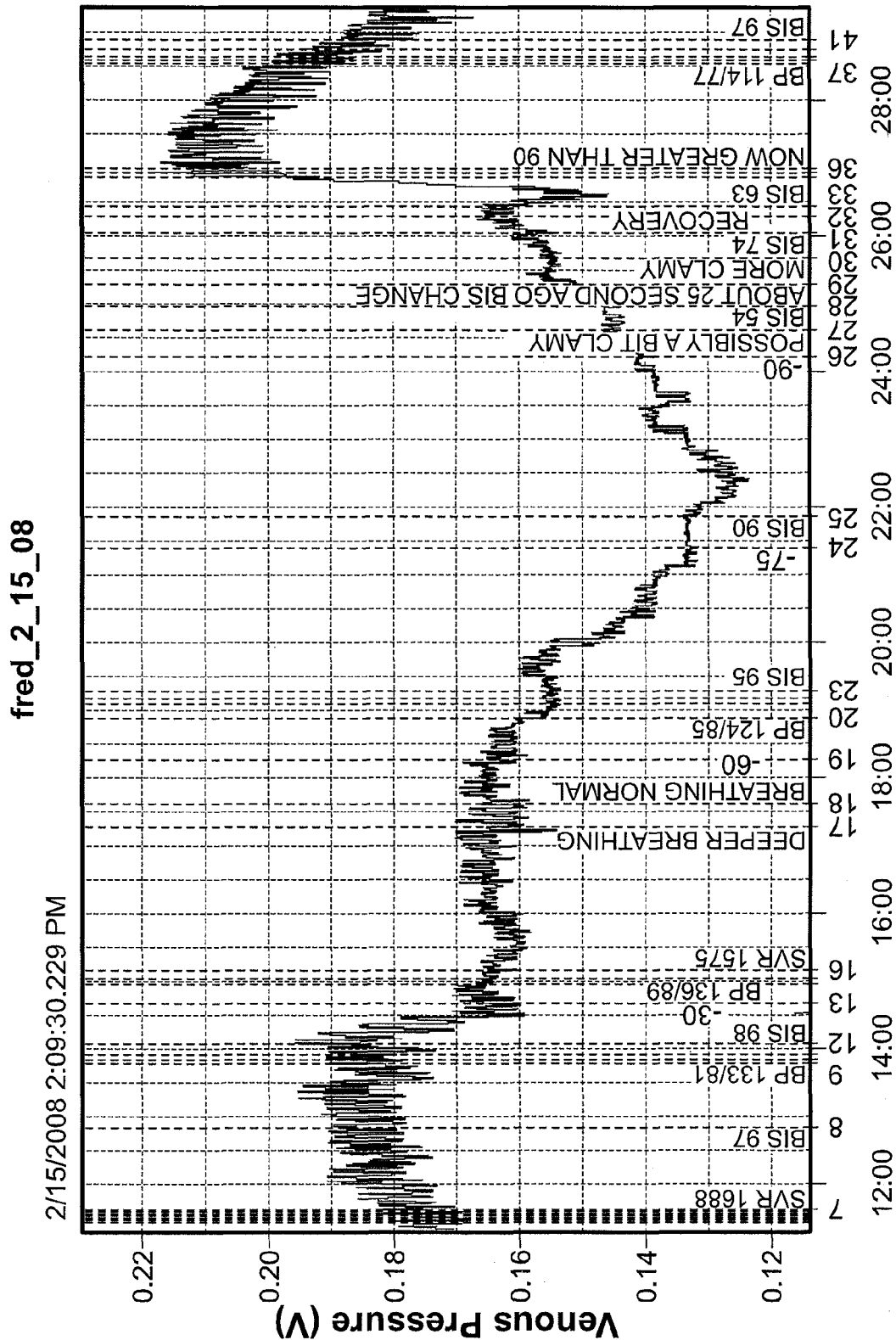
FIG. 3 depicts a PVP tracing over the course of eight (8) minutes during a LBNP experiment. A reduction in both PVP and in VIV of PVP can be observed.
Figure 10:
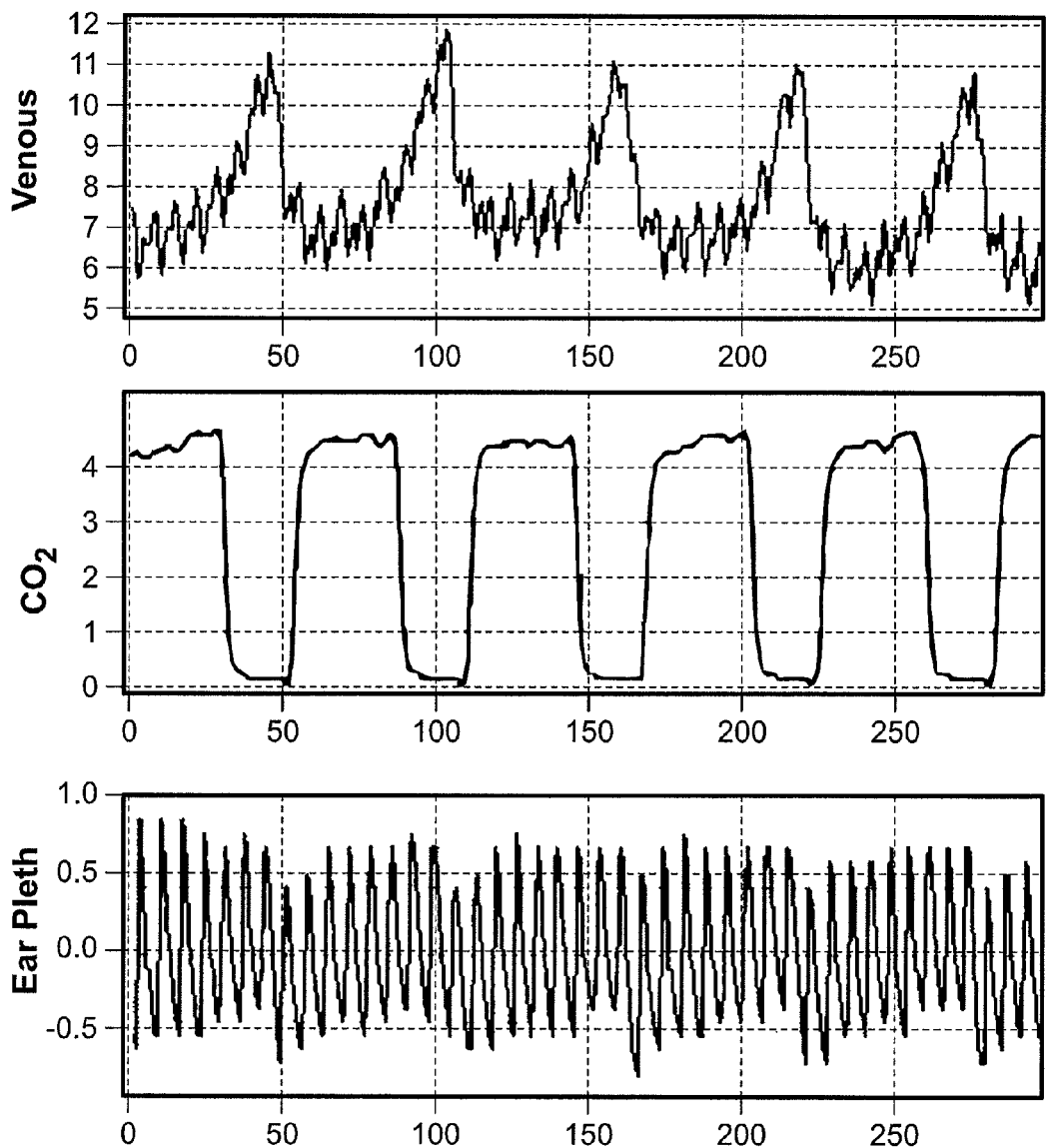
FIG. 10 depicts the normal morphology of a peripheral venous waveform during anesthesia with positive pressure ventilation. Capnogram and photoplethysmogram are also depicted.
Figure 11:
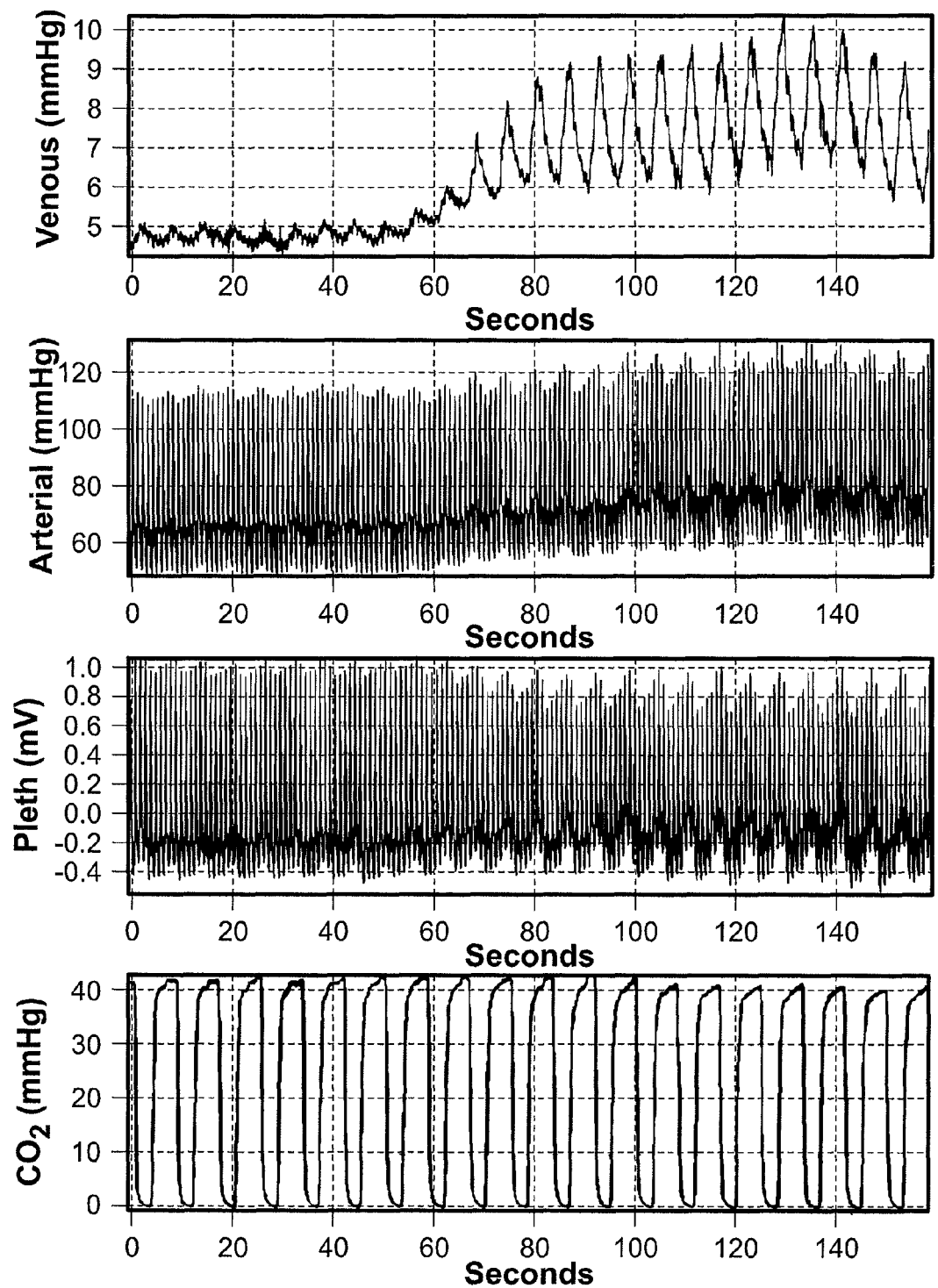
FIG. 11 depicts the onset of abdominal insufflation in a patient under general anesthesia and positive pressure ventilation, showing increase in the amplitude of venous waveform. Arterial waveform, photoplethysmogram and capnogram are also shown

Thus, a number of important observations may be drawn in support of the systems and methods presented herein:

First, the degree of VIV (either positive pressure or spontaneous) of PVP is directly related to the volume status of the patient. In other words, the higher the degree of VIV of PVP, the more "full" the patient's venous bed (i.e., since the highly compliant venous system needs to be relatively "full" to transmit changes induced by ventilation). As previously discussed, FIGS. 1 and 2 demonstrate decreases in PVP and in VIV of PVP, respectively, as a result of LBNP. Similarly, FIG. 3 also demonstrates reduction in PVP and in VIV of PVP during LBNP (see also FIGS. 10 and 11). Thus, according to the present disclosure, a decline in VIV of PVP is indicative of decreasing blood volume or relative blood volume (if the vasculature becomes dilated). Furthermore, according to the present disclosure, PVP and VIV of PVP may be used to help guide fluid replacement (colloid, crystalloid, and blood products) for a patient to achieve the goal of optimization of fluid status.

Second, VIV is not unique to PVP. In fact, VIV may also be detected for arterial pressure and for the PG signal. Importantly, in relation to volume status, changes in VIV of PVP are opposite changes in VIV of arterial blood pressure and VIV of the PG signal. For example, VIV of PVP decreases as a result of decreased blood volume while VIV of arterial blood pressure and VIV of the PG signal increased as a result of decreased blood volume. Thus, according to the present disclosure, an index may be calculated comparing VIV of PVP to one or both of: (1) VIV of arterial blood pressure, and (2) VIV of the PG signal. It is believed that such an index will result in greater sensitivity/specificity when compared to each individual parameter. As demonstrated by FIG. 2, an index comparing VIV of PVP relative to VIV of the PG signal starts at 1.3/0.7 (baseline), drops to approximately 0.6/0.8 during initial stages of LBNP (−60 mmHg), and then continues to decrease to 0.4/1.4 for later stages of LBNP. It is proposed that a ratio of less than a constant value (e.g., <1) is indicative of hypovolemia.

Figure 4:
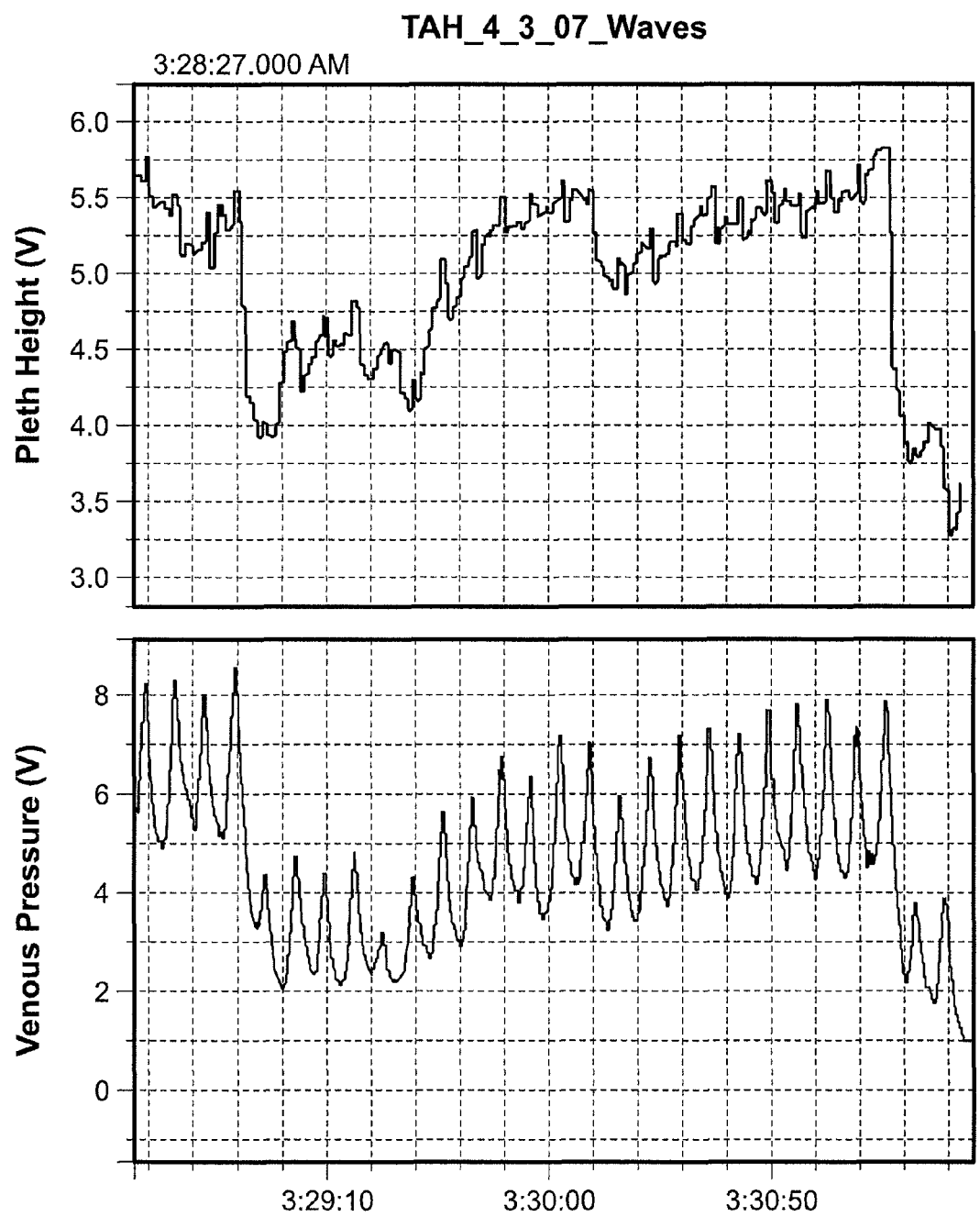
FIG. 4 depicts changes in each of PVP and the PG signal as a result of vasoconstriction.

Third, arterial vasoconstriction, similar to hypovolemia, affects the PG signal, i.e., affects VIV of the PG signal. Arterial vasoconstriction does not, however, cause a pronounced decrease in VIV of PVP. FIG. 4 depicts changes as a result of vasoconstriction over the course of approximately four minutes for each of the PG signal (top) and PVP (bottom). Transient vasoconstriction caused a decline in the mean value of both signals, but only reduced the VIV of the PG signal. Vasoconstriction typically may be caused by administration of a vasoconstricting drug. Thus, VIV of the PG signal may be used to monitor, e.g., the effect of medications on the vascular system and titrate dosage. Additionally, the differing VIV responses of PVP and PG (or arterial pressure) signals to hypovolemia as compared to vasoconstriction indicates that the above proposed ratios may be useful in delineating the nature of a physiologic disturbance.

Figure 5:
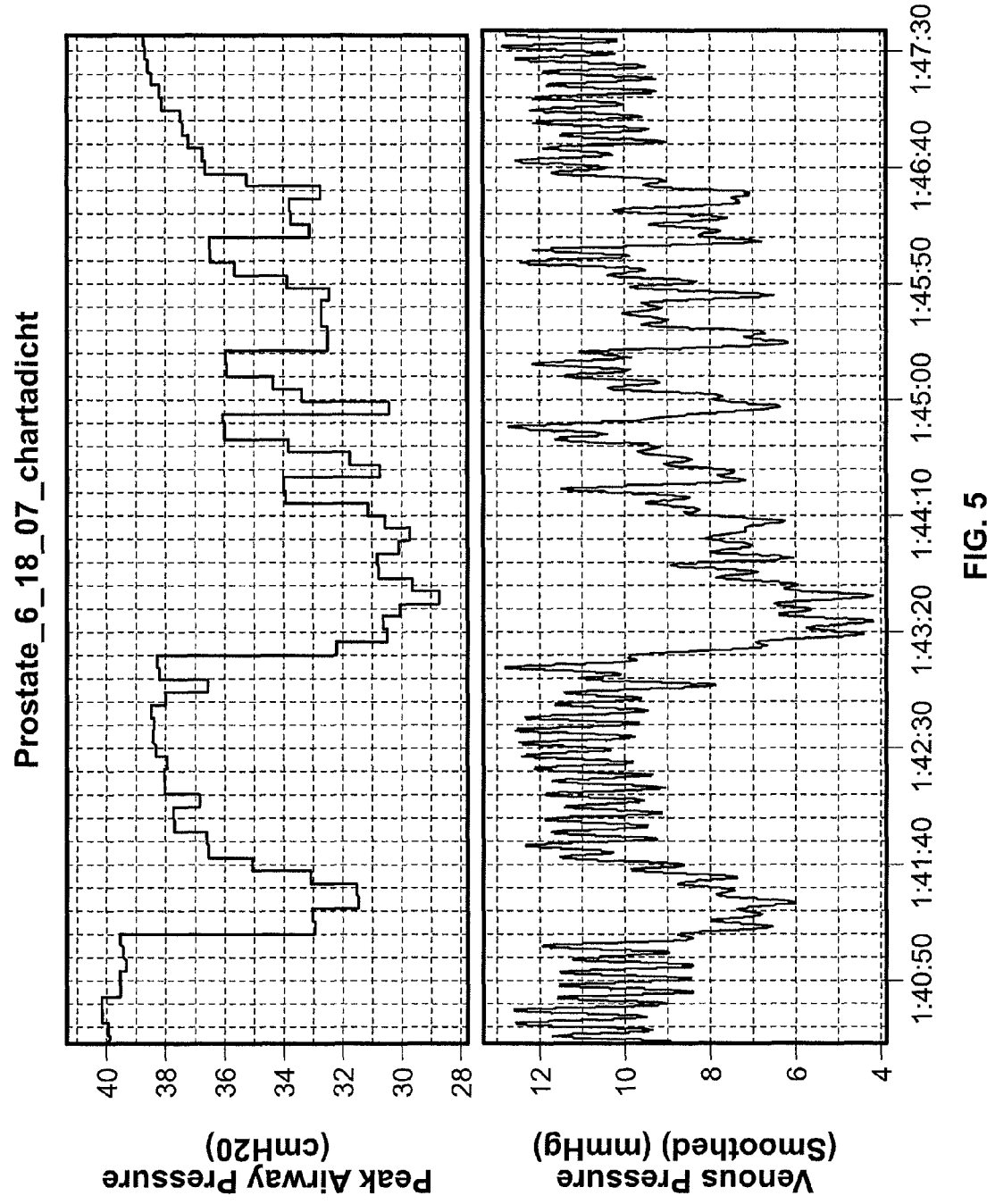
FIG. 5 depicts PVP and peak airway pressure for an intubated patient undergoing surgery.

Fourth, there exists a direct link between airway pressure and PVP. As airway pressure increases, so does PVP (venous return to the heart is slowed by increased intrathoracic pressure). Thus, during positive pressure ventilation, PVP may be used to monitor the effect of ventilation on the vascular system and assist with ventilator adjustments. Similarly, during spontaneous respiration, PVP may be used to monitor respiratory health, including asthma and heart failure, as well as treatment thereof. FIG. 5 demonstrates the correlation between PVP (bottom) and peak airway pressure (top) for an intubated patient undergoing surgery. Notably, as airway pressure drops, PVP declines and VIV is reduced.

In view of the foregoing, the following metrics may be advantageously utilized by the systems and methods of the present disclosure:

(1) Actual amplitude (in mmHG) of VIV of PVP;
(2) Relative amplitude of VIV of PVP compared to a mean PVP value;
(3) Index comparing VIV of PVP to VIV of arterial pressure; and/or
(4) Index comparing VIV of PVP to VIV of a PG signal or of a component thereof.

Coherence Analysis and Compensating for Pulmonary Effort:

As previously mentioned, systems and methods are also presented which advantageously compensate for the effect of respiratory effort (either spontaneous or positive pressure) on a cardiovascular waveform. Specifically, the systems and methods enable generation of a numeric directly related to effective blood volume independent of ventilation effort. This is important in at least two particular situations: (1) spontaneous ventilation, where breath size/strength may vary, and (2) pulmonary disease, where extra effort may be required for normal ventilation.

Isolating volume responsiveness from pulmonary effort is achieved by combining a cardiovascular waveform (e.g., a PG signal, PVP signal, etc), with a respiratory signal (such as a respiratory band, airway pressure, $CO_2$, thoracic bio-impedance, etc.). More particularly, in the spectral-domain, the power spectrum of the cardiovascular waveform $P(\omega)$ is multiplied by a respiratory power spectrum $R(\omega)$. Thus, the resulting waveform is large at those frequencies ($\omega$) where both the power spectrum of the cardiovascular waveform and the power spectrum of the respiratory signal are large and is small at those frequencies where either or both are small. The resulting waveform is then integrated over a range of respiratory frequencies (e.g., from 0.1 Hz to 0.5 Hz), thereby generating a numeric $C_p$ directly related to effective blood volume independent of ventilation effort.

It is noted that the respiratory power spectrum $R(\omega)$ may advantageously be normalized prior to multiplication. Thus, a normalized respiratory power spectrum $R_n(\omega)$ may be calculated such that its integral over the respiratory frequencies is equal to 1. In exemplary embodiments $R_n(\omega)$ may be calculated as:

$$C_p = \int_{.1}^{.5} P(w) * R_n(w) dw = \int_{.1}^{.5} P(w) * \frac{R(w)}{\int_{.1}^{.5} R(w')dw'} dw = \frac{\int_{.1}^{.5} P(w) * R(w) dw}{\int_{.1}^{.5} R(w')dw'}$$

wherein:

$$R_n(w) = \frac{R(w)}{\int_{.1}^{.5} R(w')dw'}$$

Alternatively, $R_n(\omega)$ may be calculated as:

$$R_n(w) = \frac{R(w)}{\sqrt{\int_{.1}^{.5} (R(w'))^2 dw'}}$$

It is noted that relative changes within a single patient remain unaffected by the specific normalization value selected.

It is further noted that the cardiovascular waveform power spectrum $P(\omega)$ may also be advantageously normalized prior to multiplication. Thus, e.g., $C_p$ may equal the integral of $P_n(\omega)*R_n(\omega)$ instead of $P(\omega)*R_n(\omega)$.

In the event there is only a single respiratory frequency, then $R_n(\omega)$ becomes an off-center δ function, where $R_n(\omega)=\infty$ at one value and 0 at all others. For this situation, $C_p$ may be calculated as:

$$C_p = \int_{.1}^{.5} P(w) * R_n(w) dw = \int_{.1}^{.5} P(w) * \partial(w - c) dw = P(c)$$

Thus, $C_p$ equals the value of the cardiovascular waveform power spectrum at the respiratory frequency. It is noted that for a wider range of respiratory frequencies, $C_p$ will correspond to the total power spectral intensity due to respiration.

According to the present disclosure, $C_p$ may advantageously be utilized to compensate for changes in the cardiovascular waveform due to pulmonary effort. This technique works for spontaneous respiration and involves only relatively simple computations. Alternative mathematical techniques, however, may also be used. Thus, a magnitude-squared coherence (MSC) function may be calculated in comparing the cardiovascular waveform to the respiratory signal. Similarly, a signal-to-noise ratio (SNR) may be calculated in comparing the cardiovascular waveform to the respiratory signal. It is noted that the MSC function and the SNR may be advantageously integrated over the respiratory frequencies to better reflect phase differences between the cardiovascular waveform and respiratory signal. Coherence analysis may also include computation of a correlation coefficient.

Hypovolemia in the PG Signal:

The impact of respiration on the PG signal during hypervolemia is also advantageously disclosed herein. (It is noted that the impact of respiration on the PG signal due to hypovolemia was previously described in the Shelley publication). The impact of respiration on the PG signal differs markedly during hypovolemia as compared to during hypervolemia. FIGS. 6-9 demonstrate different responses of the PG signal to hypovolemia at different frequencies (including at multiples of the respiratory and cardiac frequencies). Notably, respiration timing is also affected by the onset of hypovolemia.

Figure 6:
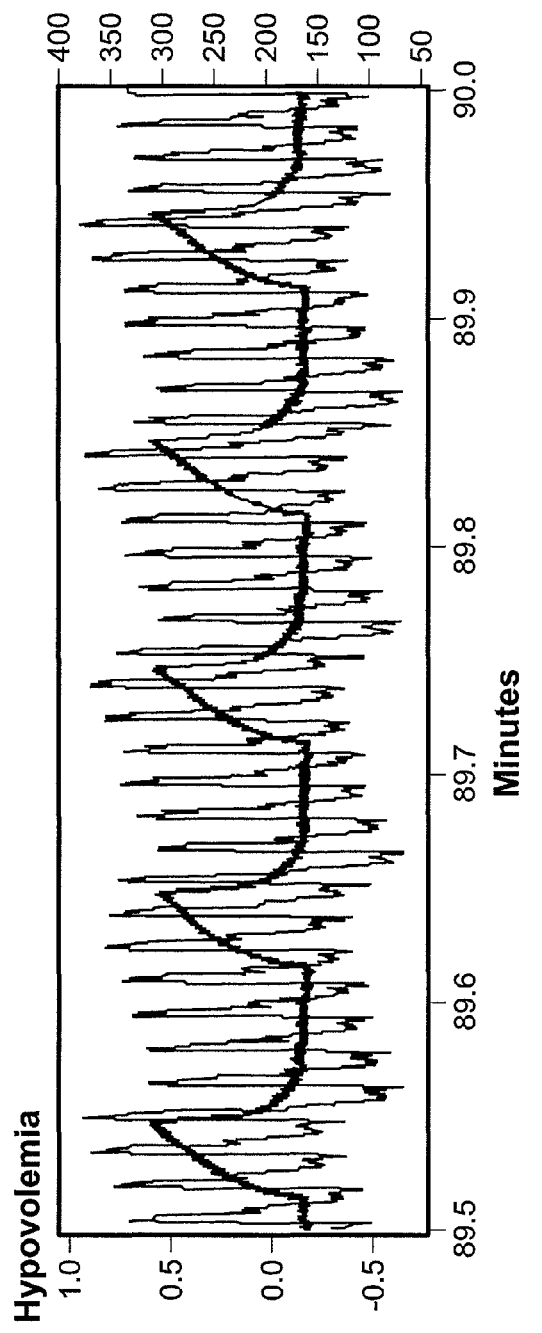
FIG. 6 depicts how the venous component of the PG signal is affected by each of hypovolemia and hypervolemia.
Figure 6:
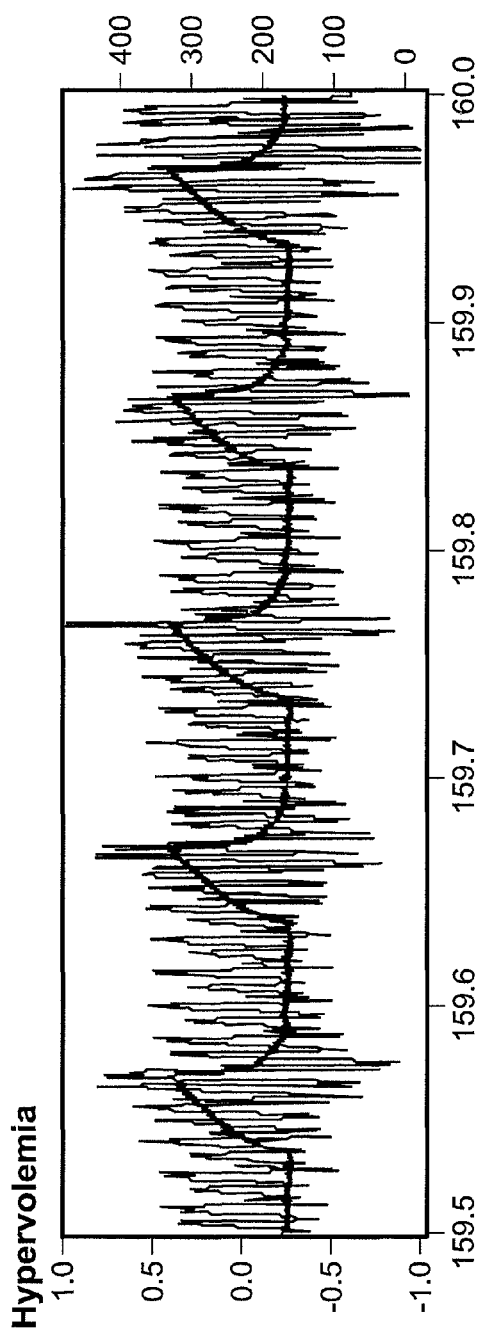

FIG. 6 illustrates how the venous component of the PG signal is affected by each of hypovolemia (top) and hypervolemia (bottom). Data was obtained during a prostatectomy wherein there was pronounced blood loss (hypovolemia) followed by aggressive fluid replacement (leading to hypervolemia). As depicted, hypovolemia induced a shift in the DC component with each breath, with only a small venous wave at the nadir of the PG waveform. In contrast, hypervolemia (with the onset of pulmonary edema) caused the appearance of a large venous pulse such that the tracing had three (3) times as many peaks despite a similar heart rate. The height of the peaks actually approaches that of the AC component. Additionally, it should be noted that the superimposed respiratory tracing enables one to identify a much faster response to ventilation during hypovolemia, such that assessment of phase differences between the changes in respiratory pressure and/or flow during the course of a breath vs. the changes in the plethysmographic signal enable assessment of relative volume status. Thus, a slower response to ventilation may be indicative, e.g., of hypervolemia.

Figure 7:
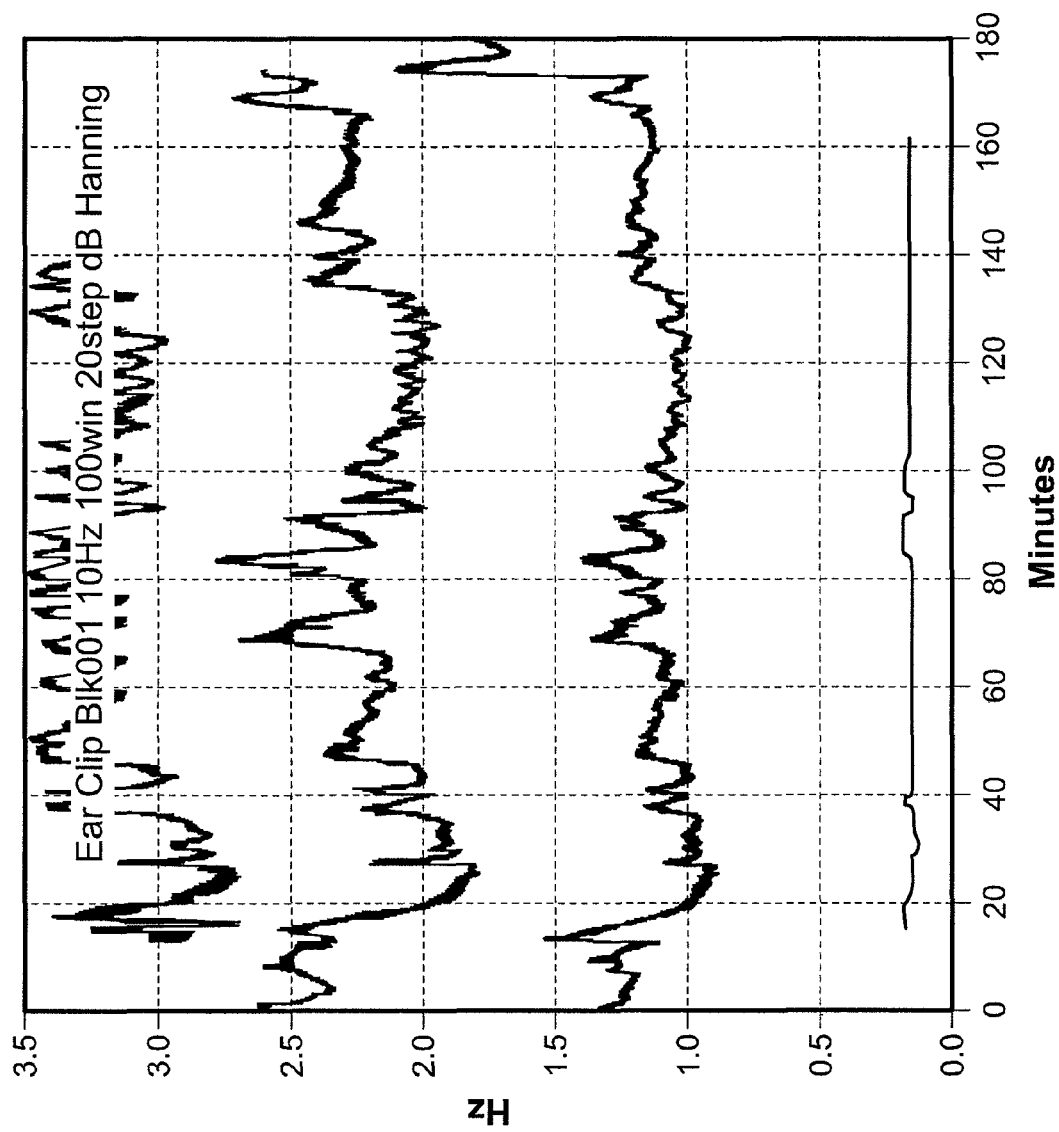
FIG. 7 depicts the impact of the changes in FIG. 6 on the power spectra of the PG signal using joint time-frequency analysis.
Figure 8:
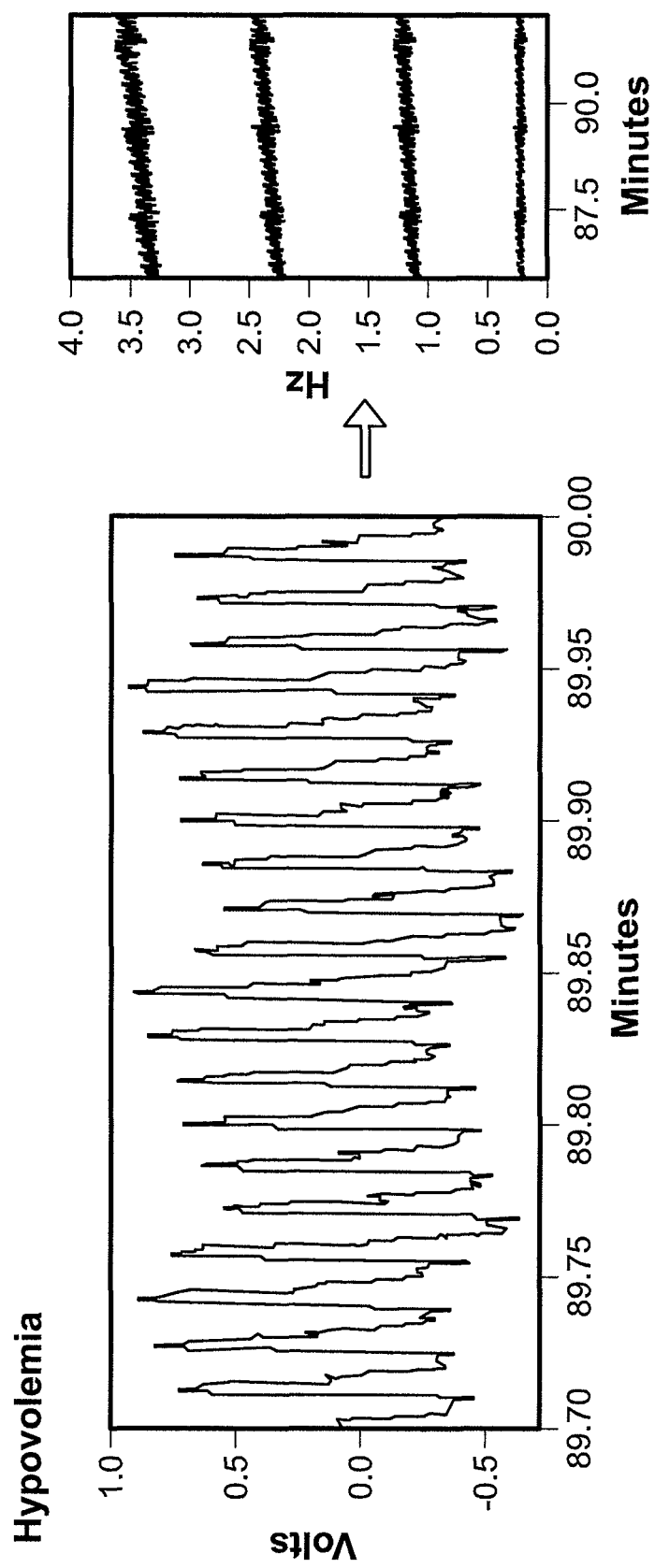
FIG. 8 depicts a small PG segment during hypovolemia and hypervolemia from the same subject as in FIG. 7. Joint time-frequency power spectra illustrate oscillatory intensity at multiples of the cardiac signal.
Figure 8:
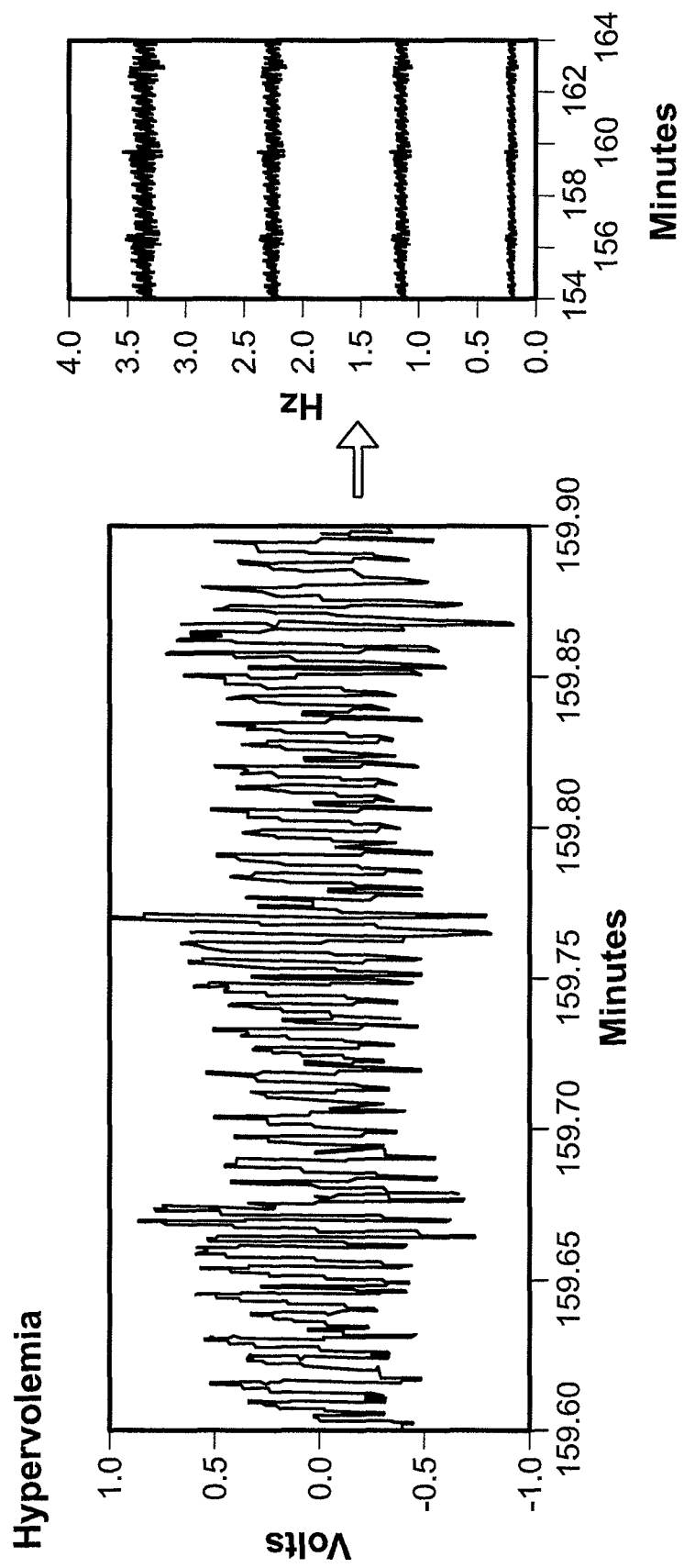
Figure 9:
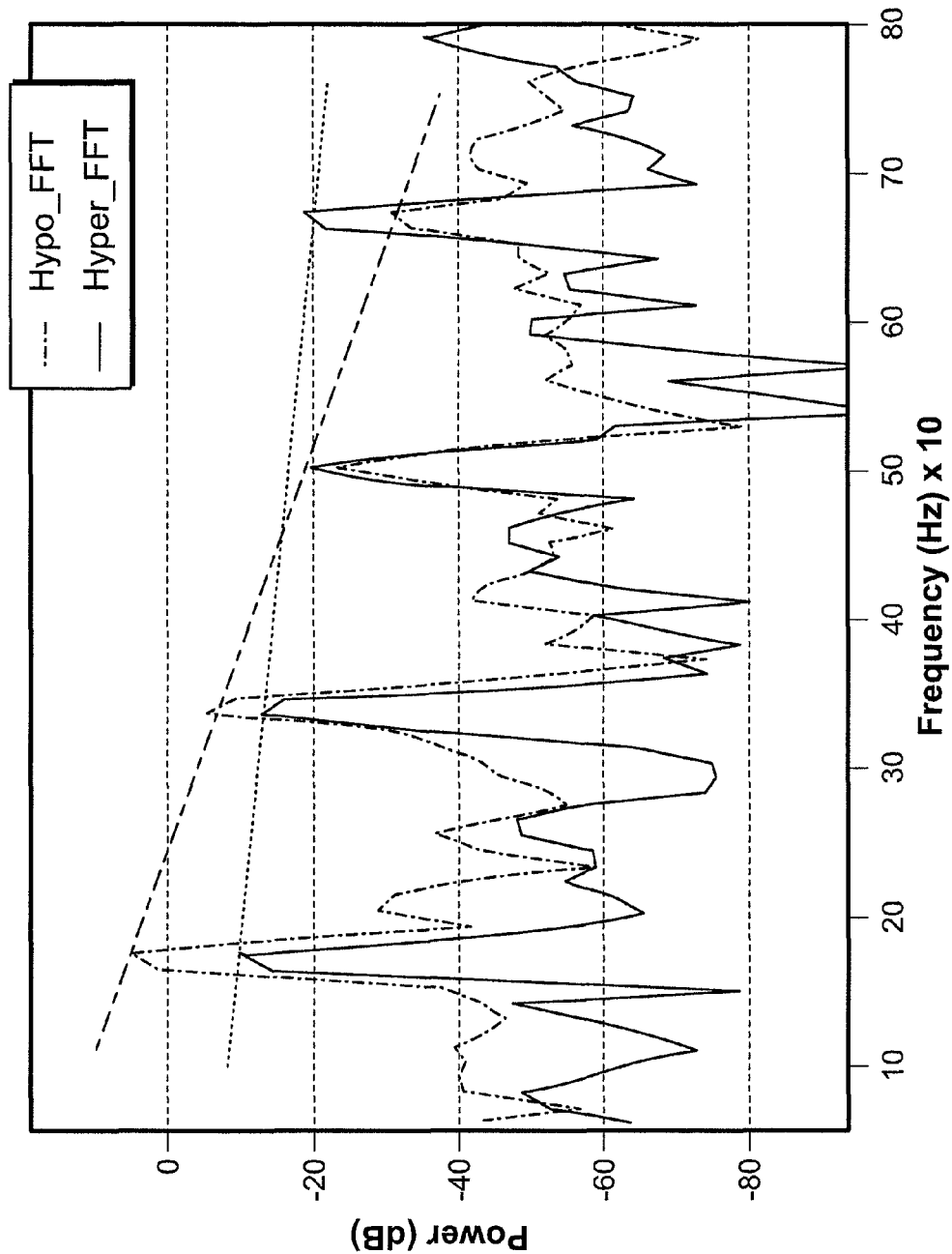
FIG. 9 depicts differences between hypovolemia and hypervolemia with respect to PG signal power at multiples of the cardiac signal.

Referring now to FIG. 7, the impact of the changes in FIG. 6 on the power spectra of the PG signal are depicted using joint time-frequency analysis. The subject was hypovolemic at 90 minutes and received extensive fluid replacement for the ensuing 70 minutes, leading to hypervolemia (with pulmonary edema). Most notable is the development of power (new lines) at secondary frequencies (side bands) near the heart rate (1 Hz) at 140-160 minutes and the increased intensity of the JTFA tracing at 2 and 3 times the pulse rate, consistent with the prominent venous signal during this period of hypervolemia. During both states, multiple spectral lines are seen at multiples of the respiratory frequency because both the arterial and venous components of the waveform are affected. The change in pulsatile venous component with each heart beat is much greater during hypervolemia. This is translated into power, not only at the pulse rate but also at multiples of the heart rate. Overall, there is an orderly shift of power to the higher frequencies.

System Implementations:

It is explicitly contemplated that the disclosed systems and methods may be carried out, e.g., via a processing unit and/or system having appropriate software, firmware and/or hardware. As previously noted, a detection device may be used to obtain a waveform of the peripheral vasculature. Thus, in exemplary embodiments, the disclosed system may include an interface for communicating with an external processing unit, e.g., directly or over a network. The external processing unit may, for example, be a computer or other stand alone device having processing capabilities. Thus, in exemplary embodiments, the external processing unit may be a multi-function unit, e.g., with the ability to communicate with and process data for a plurality of measurement devices. Alternatively, the disclosed system may include an internal or otherwise dedicated processing unit, typically a microprocessor or suitable logic circuitry. A plurality of processing units may, likewise, be employed. Thus, in exemplary embodiments, both dedicated and external processing units may be used.

The processing unit(s) of the present disclosure generally include means, e.g., hardware, firmware and/or software, for carrying out one or more of the disclosed methods/processes of calibration/normalization. In exemplary embodiments, the hardware, firmware and/or software may be provided, e.g., as upgrade module(s) for use in conjunction with existing plethysmograph devices/processing units. Software/firmware may, e.g., advantageously include processable instructions, i.e., computer readable instructions, on a suitable storage medium for carrying out one or more of the disclosed methods/processes. Similarly, hardware may, e.g., include components and/or logic circuitry for carrying out one or more of the disclosed methods/processes.

A display and/or other feedback means may also be included/provided to convey detected/processed data. Thus, in exemplary embodiments, index values may be displayed, e.g., on a monitor. The display and/or other feedback means may be stand-alone or may be included as one or more components/modules of the processing unit(s) and/or system.

In general, it will be apparent to one of ordinary skill in the art that various embodiments described herein may be implemented in, or in association with, many different embodiments of software, firmware and/or hardware. The actual software code or specialized control hardware which may be used to implement the present embodiment(s) is not intended to limit the scope of such embodiment(s). For example, certain aspects of the embodiments described herein may be implemented in computer software using any suitable computer software language type such as, for example, C or C++ using, for example, conventional or object-oriented techniques. Such software may be stored on any type of suitable computer-readable medium or media such as, for example, a magnetic or optical storage medium. Thus, the operation and behavior of the embodiments may be described without specific reference to the actual software code or specialized hardware components. The absence of such specific references is feasible and appropriate because it is clearly understood that artisans of ordinary skill would be able to design software and control hardware to implement the various embodiments based on the description herein with only a reasonable effort and without undue experimentation.

Moreover, the systems and methods of the present disclosure may be executed by, or in operative association with, programmable equipment, such as computers and computer systems. Software that causes programmable equipment to execute the methods/processes may be stored in any storage device, such as, for example, a computer system (non-volatile) memory, an optical disk, magnetic tape, or magnetic disk. Furthermore, the disclosed methods/processes may be programmed when the computer system is manufactured or subsequently introduced, e.g., via a computer-readable medium. Such a medium may include any of the forms listed above with respect to storage devices and may further include, for example, a carrier wave modulated, or otherwise manipulated, to convey instructions that may be read, decoded and executed by a computer.

It can also be appreciated that certain steps described herein may be performed using instructions stored on a computer-readable medium or media that direct a computer system to perform said steps. A computer-readable medium may include, for example, memory devices such as diskettes, compact discs of both read-only and read/write varieties, optical disk drives and hard disk drives. A computer-readable medium may also include memory storage that may be physical, virtual, permanent, temporary, semi-permanent and/or semi-temporary. A computer-readable medium may further include one or more data signals transmitted on one or more carrier waves.

A "processor," "processing unit," "computer" or "computer system" may be, for example, a wireless or wireline variety of a microcomputer, minicomputer, server, mainframe, laptop, personal data assistant (PDA), wireless e-mail device (e.g., "BlackBerry" trade-designated devices), cellular phone, pager, processor, fax machine, scanner, or any other programmable device configured to transmit and receive data over a network. Computer systems disclosed herein may include memory for storing certain software applications used in obtaining, processing and communicating data. It can be appreciated that such memory may be internal or external to the disclosed embodiments. The memory may also include any means for storing software, including a hard disk, an optical disk, floppy disk, ROM (read only memory), RAM (random access memory), PROM (programmable ROM), EEPROM (electrically erasable PROM) and other computer-readable media.

Although the present disclosure has been described with reference to exemplary embodiments and implementations thereof, the disclosed systems, and methods are not limited to such exemplary embodiments/implementations. Rather, as will be readily apparent to persons skilled in the art from the description provided herein, the disclosed systems and methods are susceptible to modifications, alterations and enhancements without departing from the spirit or scope of the present disclosure. Accordingly, the present disclosure expressly encompasses such modification, alterations and enhancements within the scope hereof.

The invention claimed is:

1. A method for compensating a cardiovascular waveform having ventilation-induced variation for pulmonary effort using a processor, the method comprising:
generating a cardiovascular waveform representing physiological characteristics of a subject;
generating a respiratory signal for the subject; and
using a processor to calculate the total power spectral intensity due to respiration, wherein the calculating the total power spectral intensity due to respiration includes:
compensating the cardiovascular waveform for pulmonary effort by multiplying the power spectrum of the cardiovascular waveform by the power spectrum of the respiratory signal; and
detecting a change in amplitude of ventilation-induced variation (VIV) in the compensated cardiovascular waveform by integrating the resulting compensated waveform over a range of respiratory frequencies, wherein the change in amplitude is reflective of a physiological change in the subject.

2. The method of claim 1, wherein the generated cardiovascular waveform is a peripheral venous pressure (PVP) waveform.

3. The method of claim 2, wherein the PVP waveform is generated from an intravenous site.

4. The method of claim 2, further comprising calculating an index comparing the amplitude of the VIV in the PVP waveform to one of: (i) an amplitude of the VIV in arterial blood pressure, and (ii) an amplitude of the VIV in a plethysmographic (PG) signal.

5. The method of claim 4, further comprising detecting hypovolemia based on the index, wherein an index value less than one (1) is indicative of hypovolemia.

6. The method of claim 4, further comprising detecting arterial vasoconstriction based on the index.

7. The method of claim 1, wherein the detecting the change in amplitude of VIV in the PVP waveform further comprises determining a relative amplitude of the VIV of the PVP compared to mean PVP.

8. The method of claim 1, further comprising monitoring fluid responsiveness based on the change in amplitude of the VIV in the compensated cardiovascular waveform.

9. The method of claim 1, further comprising detecting hypovolemia based on the change in amplitude of the VIV in the compensated cardiovascular waveform.

10. The method of claim 1, wherein the physiological change in the subject is a change in blood volume of the subject.

11. The method of claim 2, wherein a decrease in the amplitude of the VIV in the compensated cardiovascular waveform is indicative of a decrease in blood volume.

12. The method of claim 1, wherein the respiratory power spectrum is normalized prior to multiplication.

13. The method of claim 12 wherein the normalized respiratory power spectrum $R_n(\omega)$ is equal to one of:

$$R_n(w) = \frac{R(w)}{\int_{.1}^{.5} R(w')dw'} \quad (i)$$

and $$R_n(w) = \frac{R(w)}{\sqrt{\int_{.1}^{.5} (R(w'))^2 dw'}}. \quad (ii)$$

14. The method of claim 1, wherein the cardiovascular waveform power spectrum is normalized prior to multiplication.

15. A system for compensating a cardiovascular waveform having ventilation-induced variation for pulmonary effort, the system comprising:
means for generating a cardiovascular waveform representing physiological characteristics of a subject;
means for generating a respiratory signal for the subject; and
means for calculating the total power spectral intensity due to respiration,
wherein the calculating the total power spectral intensity due to respiration includes:
compensating the cardiovascular waveform for pulmonary effort by multiplying the power spectrum of the cardiovascular waveform by the power spectrum of the respiratory signal; and
detecting a change in amplitude of ventilation-induced variation (VIV) in the compensated cardiovascular waveform by integrating the resulting compensated waveform over a range of respiratory frequencies, wherein the change in amplitude is reflective of a physiological change in the subject.

16. The system of claim 15, wherein the generated cardiovascular waveform is a peripheral venous pressure (PVP) waveform.

17. The system of claim 15, wherein the respiratory power spectrum is normalized prior to multiplication.

18. The system of claim 17 wherein the normalized respiratory power spectrum $R_n(\omega)$ is equal to one of:

$$R_n(w) = \frac{R(w)}{\int_{.1}^{.5} R(w')dw'} \quad (i)$$

and $$R_n(w) = \frac{R(w)}{\sqrt{\int_{.1}^{.5} (R(w'))^2 dw'}}. \quad (ii)$$

19. The system of claim 15, wherein the cardiovascular waveform power spectrum is normalized prior to multiplication.

20. The system of claim 15, wherein the generated cardiovascular waveform is a peripheral venous pressure (PVP) waveform.

21. The system of claim 20, further comprising means for calculating an index comparing the amplitude of the VIV in the PVP waveform to one of: (i) an amplitude of the VIV in arterial blood pressure, and (ii) an amplitude of the VIV in a plethysmographic (PG) signal.

22. The system of claim 20, wherein the detecting the change in amplitude of (VIV) in the PVP waveform further comprises determining a relative amplitude of the VIV of the PVP compared to mean PVP.

* * * * *